United States Patent
Sanghvi et al.

(10) Patent No.: US 6,800,751 B2
(45) Date of Patent: Oct. 5, 2004

(54) REAGENT AND PROCESS FOR PROTECTING NUCLEOSIDE HYDROXYL GROUPS

(75) Inventors: Yogesh S. Sanghvi, Encinitas, CA (US); Emmanuel A. Theodorakis, San Diego, CA (US); Ke Wen, San Diego, CA (US)

(73) Assignees: ISIS Pharmaceuticals, Inc., Carlsbad, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 10/120,649

(22) Filed: Apr. 11, 2002

(65) Prior Publication Data

US 2003/0225262 A1 Dec. 4, 2003

(51) Int. Cl.[7] .................. C07H 21/00; C07H 21/02; C07H 21/04
(52) U.S. Cl. ............... 536/25.3; 536/25.31; 536/25.32; 536/22.1; 536/18.7
(58) Field of Search ............................ 536/25.3, 25.31, 536/25.32, 22.1, 18.7

(56) References Cited

U.S. PATENT DOCUMENTS

| | | | |
|---|---|---|---|
| 4,500,707 A | 2/1985 | Caruthers et al. | 536/27 |
| RE34,069 E | 9/1992 | Köster et al. | 536/27 |
| 5,214,134 A | 5/1993 | Weis et al. | 536/25.3 |
| 6,013,824 A | 1/2000 | Wood | 556/467 |
| 6,350,863 B1 * | 2/2002 | Shionoya et al. | 536/4.1 |

OTHER PUBLICATIONS

Chanteloup et al. Tetrahedron Letters (1994), vol. 35, pp. 877–880.*
Barton, D.H.R., et al., "The invention of radical reactions. 32. Radical deoxygenations, dehalogenations, and deaminations with dialkyl phosphites and hypophosphorous acid as hydrogen sources," *J. Org. Chem.*, 1993, 58, 6838–6842.
Barton, D.H.R., et al., "Photochemical transformations. Part XXXI.[1] Photolysis of thiobenzoic acid 0–esters. Part II.[1] General methods for the preparation of thiobenzoic acid 0–esters," *J.C.S. Perkin I*, 1973, 1571–1574.
Barton, D.H.R., et al., "A new method for the deoxygenation of secondary alcohols," *J.C.S. Perkin I*, 1975, 1574–1585.
Barton, D.H.R., et al., "Radical deoxygenations and dehalogenations with dialkyl phosphites as hydrogen atom source,"*Tetrahedron Letts.*, 1992, 33(17), 2311–2314.
Beigelman, L., et al., "Improved synthetic approaches toward 2'–0–methyl–adenosine and guanosine and their N–Acyl derivatives," *Tetrahedron*, 2000, 56, 1047–1056.

Chanteloup, L., et al., "Efficient synthesis of 2'–0–alkyl ribonucleosides using trichloroacetimidate D–ribofuranosides as ribosyl donors," *Tetrahedron Letts.*, 1994, 35(6), 877–880.
Ferreri, C., et al., "The $PdCl_2/R_3SiH$ system for the silylation of nucleosides," *Tetrahedron Letts.*, 1999, 40, 1197–1200.
Grøtli, M., et al., "Protection of the guanine residue during synthesis of 2'–0–alkylguanosine derivatives,"*J.C.S. Perkin I*, 1997, 2770–2788.
Grøtli, M., et al., "A simple method for the synthesis of 2'0–alkylguanosine derivatives," *Bioorganic & Medicinal Chemistry Letters*, 1997, 7(4), 425–428.
Gundlach, C.W., et al., "Synthesis of guanosine analogs bearing pendant alkylthiol tethers," *Tetrahedron Letts.*, 1997, 38(23), 4039–4042.
Markiewicz, W.T., et al., "Tetraisopropyldisiloxane–1,3–diyl, a group for simultaneous protection of 3'–and 5'–hydroxy functions of nucleosides," *J. Chem. Research*, 1979, (S), 24–25.
Naka, A., et al., "Palladium–catalyzed reactions of 1,1,2,2–tetraethyl– and 1,1,2,2–tetra(isopropyl) –3,4–benzo–1,2–disilacyclobut–3–ene with alkynes," *J. Organometallic Chem.*, 1996, 521, 163–170.
Roy, S.K., et al., "Efficient large scale synthesis of 2'–0–alkyl pyrimidine ribonucleosides," *Organic Process Research & Develop.*, 2000, 4(3),170–171.
Wada, T., et al., "Regioselective protection of the 2'–hydroxyl group of N–acyl–3',5'–0–di(t–butyl)silanediyl–nucleoside derivatives by use of t–BuMgCl and 2–(Trimethylsilyl)ethoxymethyl chloride,"*Tetrahedron Letts.*, 1995, 36(10), 1683–1684.
Zielinski, W.S., et al., "Oligoaminonucleoside phosphoramidates, oligomerization of dimers of 3'–amino–3'deoxy–nucleotides (GC and CG) in aqueous solution," *Nucleic Acids Res.*, 1987, 15(4), 1699–1715.
Zielinski, W.S., et al., "Autocatalytic synthesis of a tetranucleotide analogue," *Nature*, May 1987, 327, 346–347.

* cited by examiner

*Primary Examiner*—James O. Wilson
*Assistant Examiner*—Patrick Lewis
(74) *Attorney, Agent, or Firm*—Woodcock Washburn LLP

(57) ABSTRACT

Silylating reagents having a group other than a divalent oxygen separating two silyl groups provide regioselective protection of reactive groups under robust conditions, such as basic conditions used in alkylation, acylation and deoxygenation. In particular, silylating reagents having a group other than oxygen separating two silyl groups are useful for protecting two hydroxy groups of a ribonucleic or deoxyribonucleic acid. Alkylation of a 2'-hydroxy group of a ribonucleoside protected with the inventive silylating agents in the presence of an excess of a mild hindered base such as sodium HMDS may be carried out without protecting the exocyclic amine and oxo functionalities of nucleobases.

12 Claims, No Drawings

REAGENT AND PROCESS FOR PROTECTING NUCLEOSIDE HYDROXYL GROUPS

FIELD OF THE INVENTION

The present invention relates to the field of selective protection of active groups on chemical compounds. In particular, the present invention provides unique reagents and methods for selectively protecting active groups in chemical synthesis.

BACKGROUND OF THE INVENTION

It is well-known that proteins are significantly involved in many of the bodily states in multicellular organisms, including most disease states. Such proteins, either acting directly or through their enzymatic or other functions, contribute in major proportion to many diseases and regulatory functions in animals and man. For disease states, classical therapeutic methods have generally focused upon interactions with such proteins in efforts to moderate their disease-causing or disease-potentiating functions. In newer therapeutic approaches, modulation of the production of such proteins is desired. By interfering with the production of proteins, the maximum therapeutic effect may be obtained with minimal side effects. It is the general object of such therapeutic approaches to interfere with or otherwise modulate gene expression which would lead to undesired protein formation.

One method for inhibiting specific gene expression is to employ oligonucleotides, especially oligonucleotides that are complementary to a specific target messenger RNA (mRNA) sequence, to modulate, enhance or otherwise affect translation.

Transcription factors interact with double-stranded DNA during regulation of transcription. Oligonucleotides can serve as competitive inhibitors of transcription factors to modulate the action of transcription factors. Several reports describe such interactions (see Bielinska, A., et. al., Science, 1990, 250, 997–1000; and Wu, H., et. al., Gene, 1990, 89, 203–209).

In addition to functioning as both indirect and direct regulators of proteins, oligonucleotides have also found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligonucleotides, via Watson-Crick and/or Hoogsteen base pairs, to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in polymerase chain reactions (PCR) has given rise to an expanding commercial industry. PCR has become a mainstay of commercial and research laboratories, and applications of PCR have multiplied.

For example, PCR technology is used in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in PCR technology.

Laboratory uses of oligonucleotides are described generally in laboratory manuals such as Molecular Cloning, A Laboratory Manual, Second Ed., J. Sambrook, et al., Eds., Cold Spring Harbor Laboratory Press, 1989; and Current Protocols In Molecular Biology, F. M. Ausubel, et al., Eds., Current Publications, 1993. Such uses include Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA (see Book 2 of Molecular Cloning, A Laboratory Manual, ibid.) and DNA-Protein Interactions and The Polymerase Chain Reaction (see Vol. 2 of Current Protocols In Molecular Biology, ibid).

Oligonucleotides can be custom-synthesized for a desired use. Thus a number of chemical modifications have been introduced into oligonucleotides to increase their usefulness in diagnostics, as research reagents and as therapeutic entities. Such modifications include those designed to increase binding to a target strand (i.e. increase their melting temperatures, (Tm)); to assist in identification of the oligonucleotide or an oligonucleotide-target complex; to increase cell penetration; to stabilize against nucleases and other enzymes that degrade or interfere with the structure or activity of the oligonucleotides; to provide a mode of disruption (terminating event) once sequence-specifically bound to a target; and to improve the pharmacokinetic properties of the oligonucleotides.

Thus, it is of increasing value to prepare oligonucleotides and other phosphorus-linked oligomers for use in basic research or for diagnostic or therapeutic applications. Consequently, and in view of the considerable expense and time required for synthesis of specific oligonucleotides, there has been a longstanding effort to develop successful methodologies for the preparation of specific oligonucleotides with increased efficiency and product purity.

Synthesis of oligonucleotides can be accomplished using both solution phase and solid phase methods. Oligonucleotide synthesis via solution phase in turn can be accomplished using various coupling mechanisms. However, solution phase chemistry requires purification after each internucleotide coupling, which is labor-intensive and time consuming.

The current method of choice for the preparation of naturally occurring oligonucleotides, as well as modified oligonucleotides such as phosphorothioate and phosphorodithioate oligonucleotides, is via solid-phase synthesis, wherein an oligonucleotide is prepared on a polymer support (a solid support) such as controlled pore glass (CPG); oxalyl-controlled pore glass (see, e.g., Alul, et al., Nucleic Acids Research 1991, 19, 1527); TENTAGEL Support, (see, e.g., Wright, et al., Tetrahedron Letters 1993, 34, 3373); or POROS, a polystyrene resin available from Perceptive Biosystems. Solid-phase synthesis relies on sequential addition of nucleotides to one end of a growing oligonucleotide chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. The nucleotide phosphoramidites are reacted with the growing oligonucleotide using "fluidized bed" technology to mix the reagents. The known silica supports suitable for anchoring the oligonucleotide are very fragile and thus cannot be exposed to aggressive mixing. Additional methods for solid-phase synthesis may be found in Caruthers U.S. Pat. Nos. 4,415,732; 4,458, 066; 4,500,707; 4,668,777; 4,973,679; and 5,132,418; and Köster U.S. Pat. Nos. 4,725,677 and Re. 34,069.

Phosphoramidites typically have been prepared by one of three routes. In the first, a suitably protected nucleobase is reacted with a protected bis-dialkylamino phosphite compound in the presence of 1H-tetrazole or a tetrazole salt. See Nielsen, J. et al., Nucleic Acids Res. 1986, 14, 7391; Nielsen, J. et al., J. Chem. Res.(S) 1986, 26; Hamamoto, S. et al., Chem. Lett. 1986, 1401; and Nielsen, J. et al., Nucleic Acids Res. 1987, 15, 3626. This method is disadvantageous because, inter alia, tetrazole is a health hazard, and poses disposal problems due to its explosive nature.

A second method for the preparation of phosphoramidites involves reacting the 3'-hydroxyl of a nucleoside with a protected dialklyamino chloro phosphitylting reagent. See Hering, G. et al., Nucleosides Nucleotides 1985, 4, 169; and Ugi, I. et al., J. Chem. Soc. Chem. Commun. 1997, 877. This method also is disadvantageous because of the explosive nature of the phosphitylating reagent.

A third method for the synthesis of phosphoramidites involves reacting the 3'-hydroxyl of a nucleoside with a dialklyamino dichloro compound, followed by displacement of chlorine with addition of a protecting group. Tanaka, T. et al., Tetrahedron Lett. 1986, 27, 199. Phosphorodiamidites also can be prepared, for example, by the condensation of a bis(dialkylamino) chlorophosphine with a 5'-protected nucleoside according to the procedure of Grandas et al., Tetrahedron Letters 1989 30 (5) 543–546.

The chemical structures of the five 2'-dexoynucleosides and four 2'-O-alkyl nucleosides that are considered essential raw materials for the preparation of antisense drugs are shown below.

Pyrimidine Deoxy Nucleosides

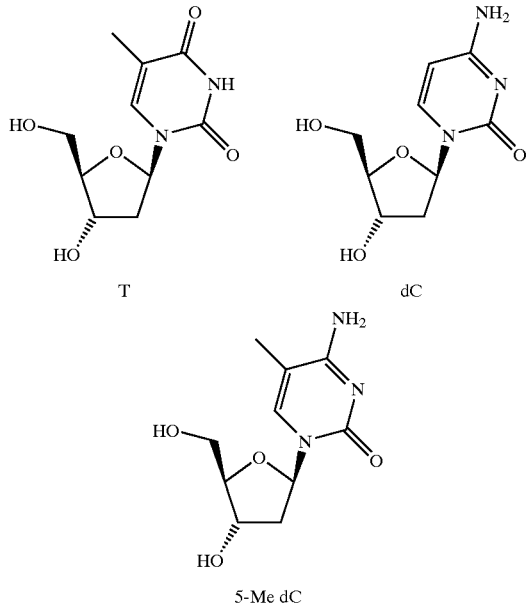

Purine Deoxynucleosides

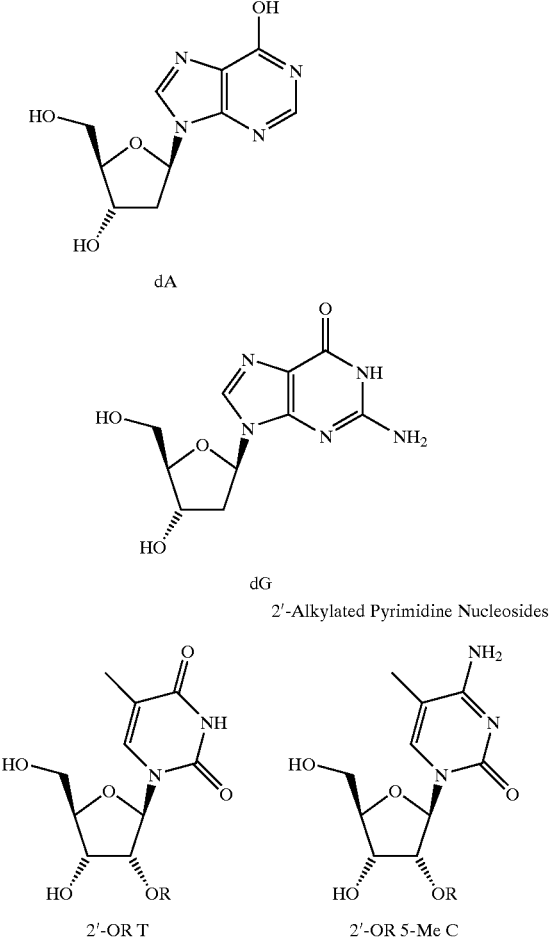

2'-Alkylated Pyrimidine Nucleosides

2'-Alkylated Purine Ribonucleosides

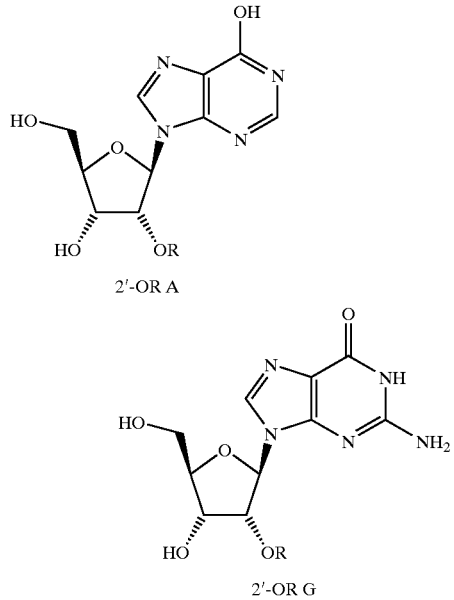

R = CH$_2$CH$_2$OMe (MOE)
R = CH$_3$ (Me)

The lengthy and inefficient harvesting process of nucleosides from fish has led to several attempts to achieve their production via a combination of chemical and enzymatic approaches. Although such strategies are used for the manufacturing of pyrimidine-containing 2'-deoxynucleosides (e.g. T, dC and 5-Me dC), they are not efficient for production of purine-containing deoxynucleosides (such as dA and dG). This problem has prompted the development of alternative processes, in which dA and dG could be obtained via chemical deoxygenation of the corresponding ribonucleotides A and G, respectively, that are easily manufactured in ton scales from yeast RNA. Nonetheless, the latter approach requires a C2' deoxygenation step that is most efficient using a 3'-, 5'-protected nucleoside precursor.

There has been increasing attention directed toward a class of 2'-O-substituted ribonucleic acids, such as 2'-O-methyl and 2'-O-methoxyethyl-substituted ribonucleic acids. Incorporation of 2'-O-alkylated ribonucleotides in antisense oligonucleotides increases both resistance of the oligonucleotides to nucleases and their thermal stability with complementary mRNA. See E. L. Ruff et al., Journal of Organic Chemistry, 1996, 61, 1547–1550;, H. Cramer et al., Helvetica Chimica Acta, 1996, 79, 2114–2136. As a result, considerable effort has been directed toward investigation of 2'-O-alkylated nucleoside-containing oligonucleotides. As the 2'-O-alkylated nucleosides represent more than 60% of the cost of raw materials in the synthesis of the respective oligonucleotides, the reduction in cost of 2'-O-alkylated nucleosides is of great importance for the further investigation and exploitation of these useful nucleosides.

Preparation of 2'-O-alkylated nucleosides requires alkylation of the 2'-OH of the corresponding nucleosides. The 2'-O-alkylation process is problematic and inefficient, especially for large-scale manufacturing, and particularly where the 2'-O-alkylated nucleoside is a purine nucleoside, such as 2'-methyladenosine (2'-Me A), 2'-methoxyethyladenosine (2'-MOE A), 2'-methyl guanosine (2'-Me G), or 2'-methoxyethoxyguanosine (2'-MOE G). P. Martin, Helvetica Chimica Acta 1995, 78, 486–504; U. Legorburu et al., Tetrahedron 1999, 55, 5635–5640.

The problems associated with the production of 2'-deoxygenated and 2'-O-alkylated purine nucleosides have been addressed by selective protection of the 3'- and 5'-hydroxyl groups. Heretofore, the most convenient protecting group for such protection has been tetraiosopropyldichlorodisiloxane (1, TIPDSCl$_2$), also known as Markiewicz reagent.

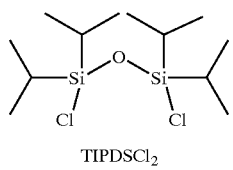

TIPDSCl$_2$

Despite the advantages of TIPDSCl$_2$, its high cost and its fragility during basic treatment make it incompatible with the conditions necessary for alkylation at the C2'-oxygen of ribonucleosides. Due to these limitations, TIPDSCl$_2$ is not generally used during the manufacture of 2'-O-alkylated ribonucleosides.

There is thus a need for a protecting group that is capable of protecting the 5'- and 3'-hydroxyl groups of a nucleoside under the basic conditions required for 2'-O-alkylation of ribonucleosides.

There is also a need for an economical protecting group that is capable of protecting the 5'- and 3'-hydroxy groups of a nucleoside during 2'-deoxygenation process in the synthesis of deoxynucleotides.

There is also a need for a protecting group that is capable of protecting multiple reactive groups during synthesis.

There is also a need for a protecting group that is capable of protecting reactive groups under a variety of conditions.

There is also a need for an improved process of selectively alkylating the 2'-hydroxyl of a nucleoside.

There is also a need for an improved process of deoxygenating a nucleoside at the 2'-position.

There is also a need for an improved process of selectively protecting one or more reactive groups on a chemical compound during organic synthesis.

There is also a need for processes of synthesizing protective groups capable of protecting two reactive groups on a nucleoside.

There is also a need for 3',5'-diprotected nucleoside intermediates useful in the production of 2'-deoxy and/or 2'-modified nucleosides.

There is further a need for an improved electrophile for preparing 2'-O-methyl nucleosides.

SUMMARY OF THE INVENTION

The foregoing and other needs are met by embodiments of the present invention, which provide a process of using a compound of the formula I to protect one or more active groups on a precursor, said compound of formula I being:

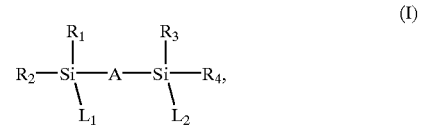

(I)

wherein A is a moiety other than O; each of $L_1$ and $L_2$ is independently a leaving group; and each of $R_1$–$R_4$ is independently a substituent, or two of $R_1$–$R_4$ taken together on the same or different Si form a silicon-containing ring; said process comprising a step for reacting the compound of formula I with said precursor to form a protected intermediate, said precursor having at least one reactive group.

The foregoing and other needs are further met by embodiments of the present invention, which provide a compound comprising a residue of a precursor having at least one reactive group coupled to a residue of a compound of formula (I), above.

The foregoing and other needs are further met by embodiments of the present invention, which provide synthetic methods of using a precursor to make a product, said precursor having at least a first and a second reactive group, the methods comprising reacting said precursor with a compound of formula (I) for a time and under conditions sufficient to protect said first reactive group, whereby a protected intermediate is formed, subjecting the protected intermediate to conditions and/or contacting said intermediate with at least one reagent for acting on the second reactive group to produce a protected product, and deprotecting the protected product to form the product.

The foregoing and other needs are further met by embodiments of the present invention, which provide synthetic methods of using a precursor to make a product, said precursor having at least a first and a second reactive group, the methods comprising reacting said precursor with a compound of formula (I) for a time and under conditions sufficient to protect said first reactive group, whereby a protected intermediate is formed, subjecting the protected intermediate to conditions and/or contacting said intermediate with at least one reagent for acting on the second reactive group to produce a protected product, and deprotecting the protected product to form the product, wherein the conditions and/or reagents for acting on the second reactive group remove the reactive group.

The foregoing and other needs are further met by embodiments of the present invention, which provide synthetic methods of using a precursor to make a product, said precursor having at least a first and a second reactive group, the methods comprising reacting said precursor with a compound of formula (I) for a time and under conditions sufficient to protect said first reactive group, whereby a protected intermediate is formed, subjecting the protected intermediate to conditions and/or contacting said intermediate with at least one reagent for acting on the second reactive group to produce a protected product, and deprotecting the protected product to form the product, wherein the conditions and/or reagents for acting on the second reactive group alkylate the reactive group.

The foregoing and other needs are met by embodiments according to the present invention, which provide compounds of the formula (II):

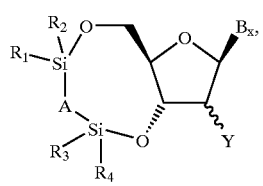

(II)

wherein A is a moiety other than O and $R_1$–$R_4$ are as defined in formula I, Y is H, OH or a 2'-substituent in the arabino- or ribo-configuration and $B_x$ is a nucleobase.

The foregoing and other needs are met by embodiments according to the present invention, which provide compounds of formula III:

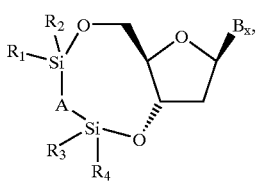

(III)

wherein each of $R_1$–$R_4$ is defined in formula I, A is a moiety other than O as defined herein and $B_x$ is a nucleobase.

The foregoing and other needs are met by embodiments of the present invention, which provide compounds of formula IV:

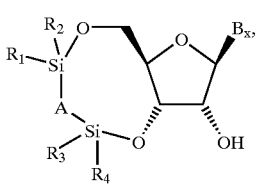

(IV)

wherein each of $R_1$–$R_4$ is defined in formula I, A is a moiety other than O as defined herein and $B_x$ is a nucleobase.

The foregoing and other needs are met by embodiments of the present invention, which provide compounds of formula V:

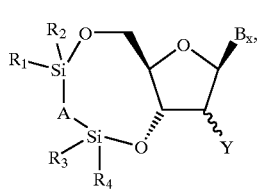

(V)

wherein each of $R_1$–$R_4$ is defined in formula I, A is a moiety other than O as defined herein, Y is a 2'-deoxy-2'-substituent in the ribo- or arabino-configuration and $B_x$ is a nucleobase.

The foregoing and other needs are met by embodiments according to the present invention, which provide compounds of the formula (VI):

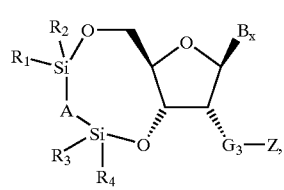

(VI)

wherein A is a moiety other than O and $R_1$–$R_4$ are as defined in formula I above, $B_x$ is a nucleobase, $G_3$ is S, O or $NR_5$, $R_5$ is H or alkyl, and Z is a 2'-O-substituent.

The foregoing and other needs are met by embodiments according to the present invention, which provide compounds of formula VII:

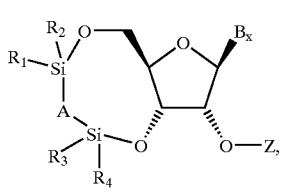

(VII)

wherein each of $R_1$–$R_4$ is alkyl, Z is a 2'-O-substituent, A is a moiety other than O as defined herein and $B_x$ is a nucleobase.

The foregoing and other needs are met by embodiments of the present invention, which provide compounds of formula VIII:

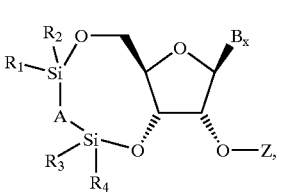

(VIII)

wherein each of $R_1$–$R_4$ is lower alkyl, Z is lower alkyl, substituted lower alkyl, or lower acyl or substituted lower acyl, A is a moiety other than O as defined herein and $B_x$ is a nucleobase.

The foregoing and other needs are met by embodiments of the present invention, which provide compounds of formula

IX:

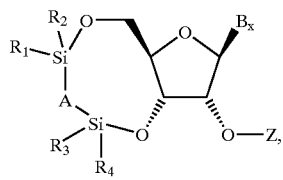

wherein each of $R_1$–$R_4$ is independently lower alkyl, Z is methyl or methoxyethyl, A is $CH_2$, and $B_x$ is a nucleobase.

The foregoing and other needs are met by embodiments of the present invention, which provide methods of preparing a compound of the formula:

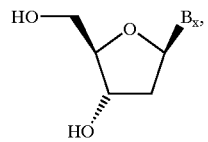

wherein $B_x$ is a nucleobase,
said method comprising reacting a ribonucleoside of formula:

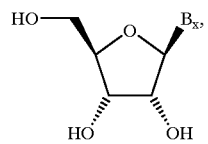

wherein $B_x$ is a nucleobase,
with a compound of formulas I to form a compound of formula IV, performing one or more steps for removing the 2'-OH to form a compound of one of the formulae III, and removing the bis-silyl protecting group to form the compound of formula IX.

The foregoing and other needs are further met by a process of making a 2'-alkylated ribonucleoside of the formula X:

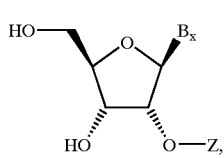

wherein $B_x$ is a nucleobase and Z is a 2'-O-substituent, such as alkyl, substituted alkyl, acyl or protected acyl,
said process comprising the steps of:
reacting a ribonucleoside, with a bis-silyl compound of formula I, to form a protected intermediate of one of formulae IV,
reacting the protected intermediate with a compound of the formula X-Z, wherein X is a leaving group and Z is a 2'-O-substituent to form a protected product of formula VII or VIII, above, and then removing the bis-silyl protecting group to provide the compounds of formula X.

The foregoing and other needs are further met by embodiments of the present invention, which provide methods of manufacturing substituted nucleosides of formula X, said methods comprising reacting a compound of the formula:

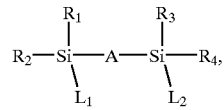

wherein A is a linking moiety, such as O or a moiety other than O, and $R_1$–$R_4$ and $L_1$ and $L_2$ are all defined in formula I,
with a nucleoside to form a 5',3'-protected nucleoside of the formula:

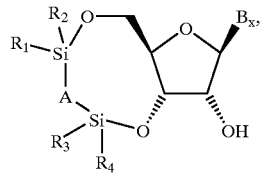

wherein A, $R_1$–$R_4$ and $B_x$ are as defined above,
reacting the 5',3'-protected nucleoside with a compound of the formula:

X-Z, wherein X is a leaving group and Z is a 2'-O-substituent, such as alkyl, substituted alkyl, acyl or substituted acyl,
in the presences of a mild hindered base or a salt thereof, to form a protected intermediate of the formula:

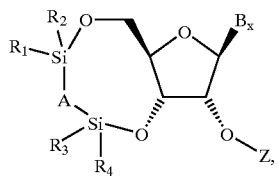

and removing the 5',3'-protective group to produce the product of formula X.

The foregoing and other objects are further met by embodiments of the present invention, which provide a method of making a 2'-O-methyl nucleoside, the process comprising reacting a ribonucleoside with a silylating agent of formula I to form a protected intermediate of formula IV, (wherein Z is $CH_3$), reacting the protected intermediate with an electrophile in the presence of a mild hindered base, and removing the protecting group to produce a 2'-O-methyl nucleoside. In some preferred embodiments of the present invention, the mild hindered base is hexamethyldisilazane (HMDS) or a salt thereof. In some especially preferred embodiments, the mild hindered base is sodium HMDS (NaHMDS). In some preferred embodiments, the electrophile is a methyl halide. In especially preferred embodiments of the invention, the electrophile is methyl chloride ($CH_3Cl$).

The foregoing and other objects are further met by embodiments of the present invention which provide methods of manufacturing compounds according to formula (I), as further described herein.

DETAILED DESCRIPTION OF THE INVENTION

The present invention provides a novel bis-silyl protecting group for protecting one or more reactive groups of a chemical compound during organic synthesis. The bis-silyl protecting group according to the present invention may introduced using a bis-silyl reagent of the formula I:

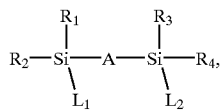
(I)

wherein A is a moiety other than oxygen, each of $L_1$ and $L_2$ is independently a leaving group; and each of $R_1$–$R_4$ is independently a substituent, or two of $R_1$–$R_4$ are taken together on the same or different Si form a silicon-containing ring to protect one or more protective groups on a chemical compound. The process of introducing the bis-silyl protecting group comprises contacting the compound of formula (I) with a compound containing at least one reactive group under conditions and for a time sufficient to protect said reactive group. In this context, the process may be viewed as a process of using the compound of formula I to make a protected intermediate. Alternatively, the process introducing the bis-silyl protecting group may be viewed as a process of making the protected intermediate, using the bis-silyl reagent of formula I as the protecting reagent.

In some embodiments of the present invention, the bis-silyl reagent of formula I is one having the formula:

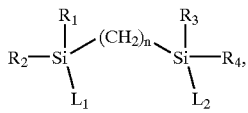

wherein n is an integer from 1 to about 12, and $R_1$–$R_4$ and $L_1$ and $L_2$ are defined herein.

In some embodiments of the present invention, the bis-silyl reagent of formula I is one having the formula:

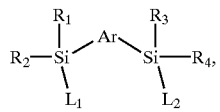

wherein A is an aryl ring or an aryl ring system, $R_1$–$R_4$ and $L_1$ and $L_2$ are as defined herein.

More specific compounds of formula I within the scope of the present invention include compounds having the formula:

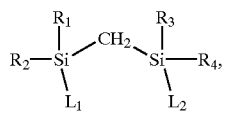

wherein $R_1$–$R_4$ and $L_1$ and $L_2$ are defined herein.

More specific compounds of formula I within the scope of the present invention also include compound having one of the formulae:

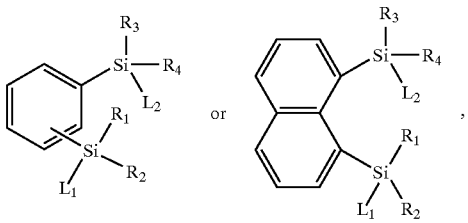

wherein $R_1$–$R_4$, $L_1$ and $L_2$ are defined herein.

The present invention provides a process of protecting the 5'- and 3'-positions of a precursor, said precursor being a nucleic acid having the formula:

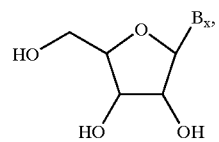

wherein $B_x$ is a nucleobase, said process comprising contacting said compound with a silylating reagent of the formula:

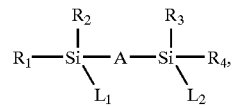

wherein $R_1$, $R_2$, $R_3$ and $R_4$ are independently alkyl, each of $L_1$ and $L_2$ is independently a leaving group, and A is a moiety other than oxygen; for a time and under conditions suitable to protect the 5'- and 3'-positions of the nucleic acid, whereby a protected intermediate is formed, said protected intermediate having the formula:

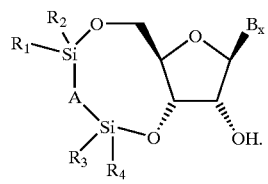

The present invention further provides a process further comprising one or more steps for alkylating or acylating the aforementioned protected intermediate to form a protected modified intermediate of the formula:

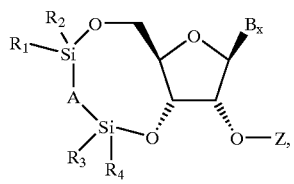

wherein Z is a 2'-O-substituent, such as alkyl, substituted alky, acyl or substituted acyl, and $R_1$–$R_4$, A is a moiety other than O and $B_x$ is a nucleobase as defined herein.

The present invention further provides a process comprising one or more steps for deoxygenating the protected intermediate or the protected modified intermediate to form a deoxygenated intermediate having the formula:

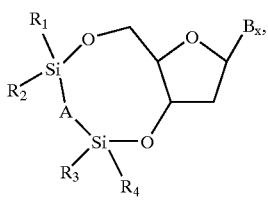

wherein $R_1$–$R_4$, A is a moiety other than O and $B_x$ is a nucleobase as defined herein.

The present invention further provides a process comprising deprotecting a protected modified intermediate or a protected deoxygenated intermediate to form a final product having one of the formulae:

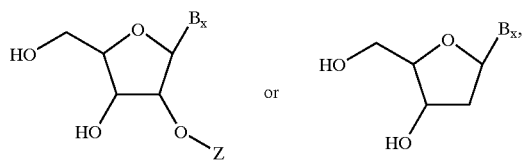

wherein $B_x$ and Z are defined herein.

The present invention further provides a process of protecting the 5'- and 3'-positions of a precursor, said precursor being a nucleic acid having the formula:

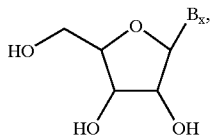

wherein $B_x$ is a nucleobase,
said process comprising contacting said compound with a silylating reagent of the formula:

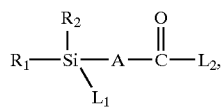

wherein each of $R_1$ and $R_2$ is independently an alkyl group, each of $L_1$ and $L_2$ is independently a leaving group, and A is alkylene, phenylene or naphthylene,
for a time and under conditions suitable to protect the 5'- and 3'-positions of the nucleic acid, whereby a protected intermediate is formed, said protected intermediate having the formula:

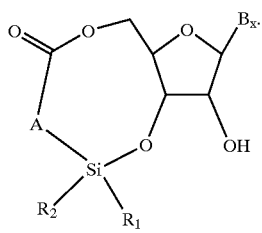

The present invention further provides a process further comprising one or more steps for alkylating or acylating the aforementioned protected intermediate to form a protected modified intermediate of the formula:

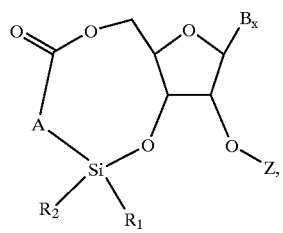

wherein Z is a 2'-O-substituent, such as an alkyl or acyl group, and $R_1$–$R_4$, A and $B_x$ are each defined herein.

The present invention further provides a process comprising one or more steps for deoxygenating the protected intermediate or the protected modified intermediate to form a deoxygenated intermediate having the formula:

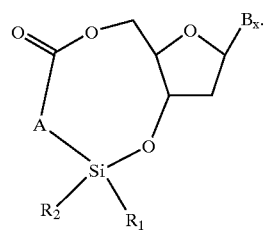

The present invention further provides a process comprising deprotecting a protected modified intermediate or a protected deoxygenated intermediate to form a final product having one of the formulae:

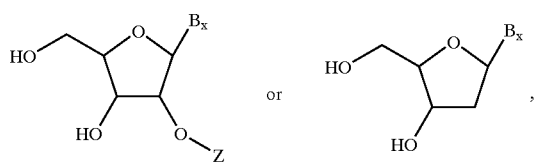

wherein $B_x$ and Z are defined herein.

The present invention further provides compounds having the formula:

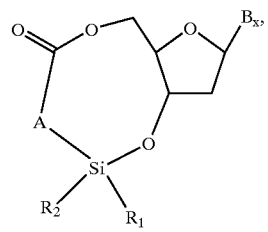

wherein $R_1$ and $R_2$ are defined in formula I and $B_x$ is a nucleobase as defined herein.

The present invention further provides compounds having the formula:

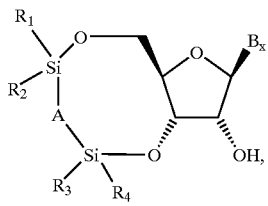

wherein $R_1$–$R_4$, A and $B_x$ are defined herein, these compounds being intermediates in the synthesis of modified nucleic acids.

The present invention further provides compound of the formula:

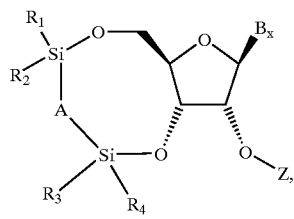

wherein $R_1$, $R_2$, $R_3$ and $R_4$ are independently alkyl, A is a moiety other than O, $B_x$ is a nucleobase and Z is a 2'-O-substituent, such as alkyl, substituted alkyl, acyl or substituted acyl, these compounds being intermediates in the synthesis if modified nucleic acids.

The present invention further provides compounds having the formula:

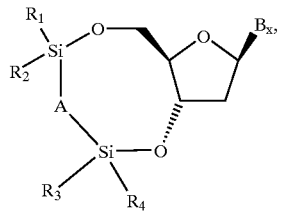

wherein $R_1$, $R_2$, $R_3$ and $R_4$ are independently alkyl, A is a moiety other than O, $B_x$ is a nucleobase and Z is a 2'-O-substituent, such as alkyl, substituted alkyl, acyl or substituted acyl, these compounds being intermediates in the synthesis of modified, especially deoxy, nucleic acids.

The present invention further provides compounds having the formula:

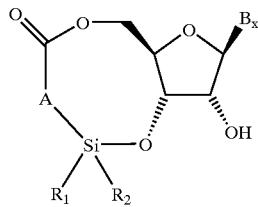

wherein $R_1$ and $R_2$ are independently alkyl, A is a moiety other than O and $B_x$ is a nucleobase, these compounds being intermediates in the synthesis of modified nucleic acids.

The present invention further provides compounds having the formula:

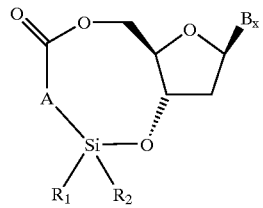

wherein $R_1$ and $R_2$ are independently alkyl, A is a moiety other than O and $B_x$ is a nucleobase, these compounds being intermediates in the synthesis of modified nucleic acids.

The present invention further provides compounds having the formula:

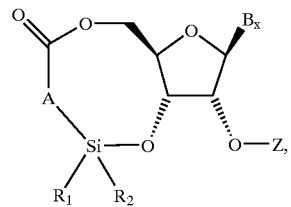

wherein $R_1$ and $R_2$ are independently alkyl, A is a moiety other than O, $B_x$ is a nucleobase and Z is a 2'-O-substituent, such as alkyl, substituted alkyl, acyl or substituted acyl, these compounds being intermediates in the synthesis of modified nucleic acids.

The present invention also provides compounds of the formula:

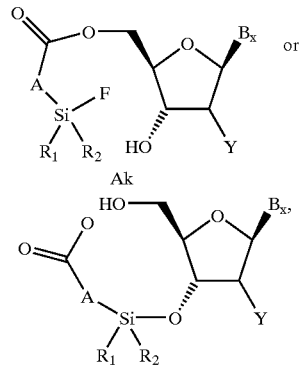

wherein $R_1$–$R_4$, A and $B_x$ are described herein, Y is H, OH (ribo or arabino), —O-Alkyl or —O-Acyl, and Ak is a $C_1$14 $C_6$ alkyl group, these compounds being useful as intermediates in the synthesis of modified nucleic acids.

The present invention also provides methods of preparing 2'-O-modified nucleosides, said methods comprising reacting a compound of the formula:

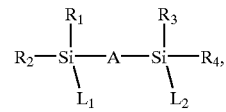

wherein A is a linking moiety, such as O or a moiety other than O, and $R_1$–$R_4$ and $L_1$ and $L_2$ are all defined in formula I, above, with a nucleoside to form a 5',3'-protected nucleoside of the formula:

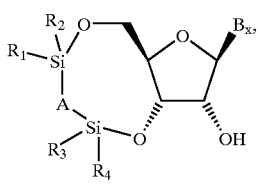

wherein A is a linking moiety, such as O or a moiety other than O, $R_1$–$R_4$ and $B_x$ are as defined above, reacting the 5',3'-protected nucleoside with a compound of the formula:

X-Z, wherein X is a leaving group and Z is a 2'-O-substituent, such as alkyl, substituted alkyl, acyl or substituted acyl, in the presences of a mild hindered base or a salt thereof, to form a protected intermediate of the formula:

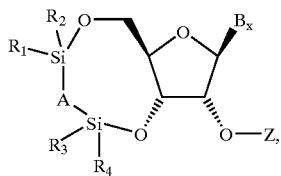

and removing the 5',3'-protective group to produce the product:

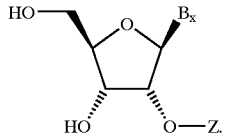

Mild hindered bases, or salts thereof, useful in the aforementioned reaction include hexamethyldisilazane (HMDS), or salts thereof. Exemplary mild hindered bases include sodium HMDS (NaHMDS) and potassium HMDS (KHMDS). An especially preferred mild hindered base is NaHMDS. A preferred electrophile, X-Z is methyl chloride ($CH_3Cl$, X being Cl and Z being $CH_3$).

In more general terms, the present invention provides a process of protecting a precursor, said precursor having at least a first reactive group, said process comprising contacting said precursor with a silylating reagent of the formula:

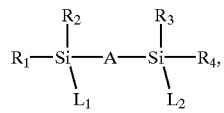

wherein A is a moiety other than O, $R_1$, $R_2$, $R_3$ and $R_4$ are independently alkyl, substituted alkyl, or two of $R_1$–$R_4$ combine to form a ring, and each of $L_1$ and $L_2$ is a leaving group, for a time and under conditions suitable to protect said first reactive group, whereby a protected intermediate is formed.

The present invention further provides processes comprising one or more steps for modifying the protected intermediate to form a protected modified intermediate. The invention also provides processes comprising one or more steps for deoxygenating the protected intermediate to form a protected deoxygenated intermediate. The present invention also provides processes comprising one or more steps for deprotecting the protected modified intermediate or the protected deoxygenated intermediate to form final products.

The present invention further provides for protecting a nucleoside or nucleoside analog having the formula:

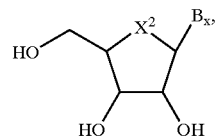

wherein $B_x$ is a nucleobase and $X^2$ is selected from the group consisting of O, S, NH, $NR^5$, $CH_2$, $CHR^6$ or $CR^7R^8$, wherein $R^5$ is alkyl, $R^6$ is alkyl, and $R^7$ and $R^8$ are alkyl or are taken together to form a carbocyclic ring.

The present invention further provides a process of protecting a precursor having at least a first reactive group, said process comprising contacting said compound with a silylating reagent of the formula:

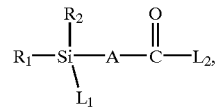

wherein A is aryl, each of $R_1$ and $R_2$ is alkyl, substituted alkyl, or $R_1$ and $R_2$ combine to form a ring, and each of $L_1$ and $L_2$ is a leaving group, for a time and under conditions suitable to protect said first reactive group, whereby a protected intermediate is formed.

The present invention further provides processes comprising one or more steps for modifying a protected intermediate to form a protected modified intermediate. The invention also provides processes comprising one or more steps for deoxygenating the protected intermediate to form a protected deoxygenated intermediate. The present invention also provides processes comprising deprotecting the protected modified intermediate or the protected deoxygenated intermediate to form final products.

The silylating reagents according to the present invention are those having the formula:

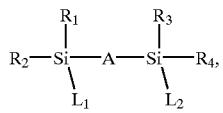

wherein A is a moiety other than O, $R_1$–$R_4$ are substituents and $L_1$ and $L_2$ are leaving groups.

The moiety A is a suitable linking moiety that acts as a spacer between the two Si atoms. Suitable moieties for linking the two Si atoms include NH, S, an alkylene chain, an aryl group (such as benzene), an aryl system (such as naphthylene), a carbocyclic ring (such as cyclopentane, cyclohexane, cycloheptane), bridged carbocyclic (bicyclo[2.2.1]heptane, bicyclo[3.2.1]octane, etc.), partially hydrogenated aryl (e.g. 1,2,3,4-tetrahydronaphthylene), heterocyclic, unsaturated heterocyclic, or heteroaryl. When A is an alkylene chain, it may be branched or straight-chain and may include, where appropriate, one or more unsaturations. Among the unsaturated alkylene chains that may be mentioned is the moiety:

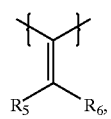

wherein $R_5$ and $R_6$ are each selected from a substituent as defined for $R_1$–$R_4$ and the brackets { } show the points of attachment of A to the Si atoms. In particular embodiments $R_5$ and $R_6$ are selected from H, $C_1$–$C_6$ alkyl, or fluoro $C_1$–$C_6$ alkyl, polyfluoro $C_1$–$C_6$ alkyl or perfluoro $C_1$–$C_6$ alkyl. In particular embodiments, A is >C=$CH_2$, The moiety A should be chosen from among those moieties that do not interfere with the silylation reaction. The A moiety should also maintain Si atoms at the proper distance apart from one another to accomplish the desired protection (e.g. 5',3'-diprotection of nucleosides). Especially suitable values for A include methylene (i.e. —$CH_2$—), 1,2-benzene, 1,3-benzene, 1,2-naphthylene, 1,8-naphthylene, etc. In some embodiments according to the present invention, the moiety A that is chosen should permit the silylating agent to protect the 5' and 3' OH groups of a nucleoside precursor. The methylene (—$CH_2$—) moiety is suitable for such uses. In other embodiments, the moiety A is chosen to permit protection of the 5' and 2' OH groups.

The A moiety may be substituted with one or more substituents that do not interfere with the silylating reaction. Among the substituents that may be mentioned are alkyl, alkenyl, alkynyl, acyl, alkanoylamino, alkanoylsulfonyl, fluoro, trifluoromethyl, alkoxyalkyl, etc. The substituents on A may be selected to impart improved solubility or regioselectivity to the protecting group, the protected intermediate, etc. For example, use of a non-ionic polar substituent may be used to improve the protecting group's solubility in a polar solvent, whereas use of bulky groups may increase the regioselectivity of the protecting group by sterically hindering certain reactions between the silylating reagent and certain reactive groups on the precursor.

The substituents $R_1$–$R_4$ may any substituents that do not interfere with the silylating reaction. For example, $R_1$–$R_4$ may be alkyl, alkenyl, alkynyl, or substituted alkyl, alkenyl or alkynyl, or $R_1$ and $R_2$ may combine to form a ring and/or $R_3$ and $R_4$ may combine to form a ring. In other embodiments, $R_1$ and $R_3$ may combine to form a ring. In some embodiments, $R_1$–$R_4$ are independently selected from methyl, ethyl, isopropyl, n-propyl, isobutyl, n-butyl, s-butyl and t-butyl. In certain embodiments, $R_1$–$R_4$ are each methyl. In other embodiments, $R_1$–$R_4$ are each isobutyl.

The leaving groups $L_1$ and $L_2$ may be any leaving group suitable for silylation chemistry. In some embodiments, $L_1$ and $L_2$ are independently selected from Cl, Br and I. In some embodiments, both $L_1$ and $L_2$ are Cl. In other embodiments, both $L_1$ and $L_2$ are Br. Other combinations are possible and are contemplated within the scope of the invention.

A preferred class of protecting groups is one in which A is methylene, $L_1$ and $L_2$ are Cl and $R_1$–$R_4$ are methyl.

Another preferred class of protecting groups is one in which A is methylene, $L_1$ and $L_2$ are Br and $R_1$–$R_4$ are methyl.

Another preferred class of protecting groups is one in which A is methylene, $L_1$ and $L_2$ are Cl and $R_1$–$R_4$ are isopropyl.

Another preferred class of protecting groups is one in which A is methylene, $L_1$ and $L_2$ are Br and $R_1$–$R_4$ are isopropyl.

Another preferred class of protecting groups is one in which A is 1,2-benzene or 1,3-benzene, $L_1$ and $L_2$ are Cl and $R_1$–$R_4$ are methyl.

Another preferred class of protecting groups is one in which A is 1,2-benzene or 1,3-benzene, $L_1$ and $L_2$ are Br and $R_1$–$R_4$ are methyl.

Another preferred class of protecting groups is one in which A is 1,2-benzene or 1,3-benzene, $L_1$ and $L_2$ are Cl and $R_1$–$R_4$ are isopropyl.

Another preferred class of protecting groups is one in which A is 1,2-benzene or 1,3-benzene, $L_1$ and $L_2$ are Br and $R_1$–$R_4$ are isopropyl.

Another preferred class of protecting groups is one in which A is 1,8-naphthylene, $L_1$ and $L_2$ are Cl and $R_1$–$R_4$ are methyl.

Another preferred class of protecting groups is one in which A is 1,8-naphthylene, $L_1$ and $L_2$ are Br and $R_1$–$R_4$ are methyl.

Another preferred class of protecting groups is one in which A is 1,8-naphthylene, $L_1$ and $L_2$ are Cl and $R_1$–$R_4$ are isopropyl.

Another preferred class of protecting groups is one in which A is 1,8-naphthylene, $L_1$ and $L_2$ are Br and $R_1$–$R_4$ are isopropyl.

When the protecting group is of the formula:

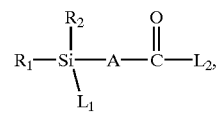

A, $R_1$, $R_2$, $L_1$ and $L_2$ each have the values set forth above.

The present inventors have found that silylating agents of the formula:

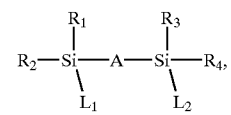

wherein A is a moiety other than O, $R_1$–$R_4$ are substituents and $L_1$ and $L_2$ are leaving groups, can be manufactured by the following method.

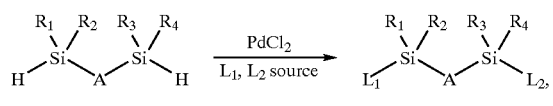

wherein $R_1$–$R_4$ are each independently a substituent, A is a moiety other than O, and $L_1$ and $L_2$ are each a leaving group. The $L_1$, $L_2$ source (leaving group source) may be one or more compounds capable of providing $L_1$ and $L_2$ to the silylating reagent. For example, where $L_1$ and $L_2$ are the same, and each is Cl, a suitable leaving group source is $CHCl_3$ or $CCl_4$. Wherein $L_1$ and $L_2$ are the same, and each is Br, a suitable leaving group source is $CH_2Br_2$. Mixtures of leaving group sources may be used to provide mixed $L_1$, $L_2$ silylating reagents. The reaction may be carried out at elevated temperatures, e.g. about 60° C. The compound $PdCl_2$ acts as a catalyst in the reaction, and may be used in less than stoichiometric quantities, e.g. about 2 mol % based on the amount of bis-silane starting material.

Compounds the bis-silane starting material of the formula:

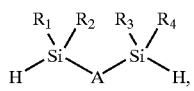

can be produced by one of the following methods.

When A is an alkylene chain, such as methylene, the starting material may be made by the reaction:

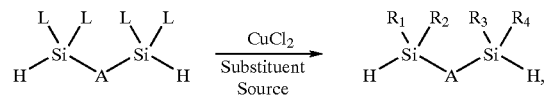

wherein each L is a leaving group, such as Cl or Br, and the substituent source is a compound having the formula RMgCl, wherein R is selected from $R_1$–$R_4$. Where $R_1$–$R_4$ are different, RMgCl is a mixture having the formula $R_1$MgCl, $R_2$MgCl, $R_3$MgCl, $R_4$MgCl. This reaction takes place in a suitable solvent, such as a polar organic solvent, e.g. THF. There action mixture may be advantageously heated, for example in the range of about 25 to about 60° C. The compound $CuCl_2$ is a catalyst in the reaction, and may be used in less than stoichiometric quantities, e.g. about 1.5 mol % based on bis-silane starting material.

Where A is an aryl group (including a heteroaryl group) the starting material may be made by the formula:

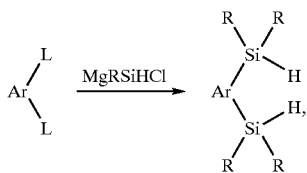

wherein each L is independently a leaving group, such as Cl or Br and each R is independently chosen from $R_1$–$R_4$ as defined above. The reaction may be advantageously carried out in a suitable solvent, such as a polar organic solvent, e.g. THF. The reaction may be carried out at elevated temperatures, e.g. about 60° C.

As can be seen from the above general description, the silylating reagents according to the present invention are generally amenable to a variety of synthetic processes in which reactive groups must be protected in order to prevent their derivatization or elimination during synthesis. Among other synthetic scenarios in which silylating reagents according to the invention may be employed include substitution, elimination, ring opening, ring closure, Diels-Alder reactions, Friedel-Crafts acylation or alkylation, oxidation, reduction, etc. In some preferred embodiments of the invention, the inventive silylating reagent is used to protect a reactive group during an alkylation or acylation reaction of a reactive group. In particular embodiments of the present invention, the inventive silylating reagent protects one or more hydroxyl groups while a hydroxyl group is alkylated or acylated. In specific embodiments of the present invention, the inventive silylating reagent is used to protect the 3'- and 5'-OH groups of a ribose or deoxyribose moiety of a nucleoside or deoxynucleoside, while the 2'-OH is available to be alkylated or acylated.

In other embodiments of the invention, the silylating reagent is used to protect one or more reactive groups during elimination of a reactive group. In particular embodiments, the inventive silylating reagent is used to protect one or more hydroxy groups, while an unprotected hydroxy group is removed via functionalization and elimination. In specific embodiments of the present invention, the inventive silylating reagent protects the 3'- and 5'-OH groups of a ribonucleic acid, while the 2'-OH is removed by elimination functionalization and deoxygenation. Examples of functional groups useful in deoxygenation reactions include 2'-O—C(S)—S-Me and —O—C(S)—O-(4-F-phenyl). Suitable methods for removing the functionalized 2'-OH moiety include the dimethylphosphite and benzoyl peroxide methodology taught by D. H. R. Barton et al. in Tetrahedron letters, Vol. 33, No. 17, pp. 2311–2314 (1992).

Suitable reactive groups to be protected by the silylating reagents and methods of the present invention include hydroxy (OH), thiol (mercapto, SH), dithionyl (S—SH), primary amino ($NH_2$), secondary amino (NHR, wherein R is an organic moiety), sulfuric acid (—O—$SO_3$H), sulfonic acid (—$SO_3$H), oxime (=NOH), hydrazine (—$NHNH_2$), amide ($CONH_2$), sulfonamide ($SO_2NH_2$), carboxylic acid (—$CO_3$H), guanine (—NHC(=NH)$NH_2$), hydrazone (=N—NH), semicarbazide (—NHNH(C=O)$NH_2$), semicarbazone (=NNH(C=O)$NH_2$). In some embodiments according to the present invention, preferred reactive groups to be protected include hydroxy, thiol and amine groups. In specific embodiments of the present invention, preferred reactive groups are hydroxy groups.

Suitable precursors for use in the present invention include nucleosides, such as ribonucleosides and 4'-desmethylribonucleosides. See Cook et al., U.S. Pat. No. 5,233,618 for suitable 4'-desmethylribonucleosides. Other suitable precursors include nucleoside analogs wherein the ring oxygen of the ribose ring has been replaced by S, NH or $CH_2$. See U.S. Pat. No. 6,001,982 for S-containing rings; U.S. Pat. No. 5,714,606 for NH-containing rings. Other suitable precursors include β-lactam rings. See U.S. Pat. Nos. 5,554,746, 5,866,691, and 5,629,152.

In some embodiments according to the present invention, a suitable precursor has the formula:

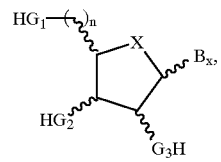

wherein $B_x$ is a nucleobase, as described herein, $G_1$, $G_2$ and $G_3$ are each independently O, S, NH, NHNH, =NNH, or $SO_3$, X is O, S, NH or $CH_2$, and n is 0, 1 or 2. In some embodiments according to the present invention, $G_1$, $G_2$ and $G_3$ are each O or S, X is O, S, NH or $CH_2$, and n is 0 or 1. In particular embodiments according to the present invention, $G_1$, $G_2$ and $G_3$ are each O or S, X is O or S, and n is 1. In specific embodiments of the invention, $G_1$, $G_2$ and $G_3$ are each O, X is O or S and n is 1

In some preferred embodiments according to the present invention, a precursor has the formula:

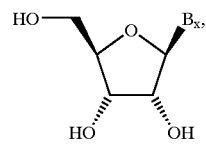

wherein $B_x$ is a nucleobase, as described herein.

While the ribonucleoside depicted above is shown in the β-D-configuration, nucleosides having other configurations may also be protected by the methods according to the present invention. Such other configurations include α-D, α-L and β-L configurations. While the nucleoside depicted above is a ribonucleoside, other sugar backbones, such as arabinose, xylose, lyxose, erythrose, threose, etc., as well as their deoxy derivatives may be protected by the silylating reagents and methods according to the present invention.

Other precursors amenable to protection with a silylating compound according to the present invention include glucocorticoids, such as alclometasone, algestone, beclomethasone, betamethasone, budesonide, chlorprednisone, clobetasol, clocortolone, cloprednol, corticosterone, cortisone, cortivazol, dexamethasone, diflucortolone, flumethasone, halometasone, etc. and analogs such as cortolone. Other precursors amenable to protection with a silylating compound according to the present invention include benzodiazepines such as chlorazepic acid, lorazepam, etc., prostaglandins, such as limaprost, luprostiol, etc., amino acids, such as serine, threonine, linatine, etc. and opioids such as morphine, nalbuphine, etc.

The silylating agents according to the present invention are used to protect one or two reactive groups on a precursor. The person having skill in the art will recognize that there are many synthetic scenarios in which it is desirable to protect reactive groups such as those noted above. In some embodiments of the present invention, the reactive groups are protected in order to perform further synthetic steps on an unprotected reactive group. Exemplary synthetic steps that can be performed on unprotected reactive groups according to the present invention include nucleophilic substitution reactions (where the reactive group acts as a nucleophile), oxidation (where the reactive group is oxidized to a higher oxidative state), reduction (where the reactive group is reduced to a lower oxidative state or eliminated altogether), elimination reactions (where the reactive group is eliminated via an E1 pathway), etc.

In some embodiments according to the present invention, the unprotected reactive group is a hydroxy or thiol group that is oxidized to form a oxo (=O) or thioxo (=S) group. Such a group may be subjected to, for example, reductive amination to produce an amine in place of a hydroxy substituent, for example at the 2'-position of a ribonucleoside.

In other embodiments according to the present invention, the unprotected reactive group may be act as a nucleophile in a nucleophilic substitution reaction. Suitable reactive groups for nucleophilic substitution include OH, SH, NH$_2$, NHNH$_2$, =NNH, SO$_3$H, etc. In particular embodiments according to the present invention, the reactive group is OH and the OH is subjected to alkylation or acylation. In specific embodiments according to the present invention, the unprotected reactive group is the 2'-OH or a ribonucleic acid that is alkylated or acylated. Suitable 2'-O-alkyl or 2'-O-acyl groups include: alkyl; alkenyl; alkynyl; alkoxyalkyl, wherein the alkyl (including the alkyl part of alkoxy), alkenyl and alkynyl may be substituted or unsubstituted, $C_1$ to $C_{10}$ alkyl or $C_2$ to $C_{10}$ alkenyl and alkynyl. Particularly preferred 2'-O-alkyl or 2'-O-acyl groups include O[(CH$_2$)$_n$O]$_m$CH$_3$, O(CH$_2$)$_m$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: O-alkaryl or O-aralkyl. Preferred modifications includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other unprotected reactive groups include carboxylic acids (which may be subjected to amidation, esterification, reductive amidation, etc.), amides (which may be reduced to produce amines, or may act as nucleophiles in a nucleophilic substitution reaction), sulfonates (which may be esterified, etc.), sulfonamides (which may act as a nucleophile), oximes (nucleophile), hydrazines and hydrazones (nucleophiles), etc. The person of skill in the art will recognize that the inventive silylating reagents are thus versatile protecting groups, suitable to protect a variety of reactive groups under a variety of reactive conditions.

The inventive silylating reagent may also be used to protect reactive groups during synthetic steps in which no other reactive group per se is involved. Exemplary reaction schemes in which protection of one or more reactive groups may be necessary include Friedel-Crafts acylation of an aryl or heteroaryl moiety, carbocation reactions, ring opening reactions (e.g. of lactams to form aminoacids, etc. Again, the versatility of the inventive silylating reagent is shown by the diversity of groups that can be protected and the variety of conditions under which the reagent can be used to protect those groups.

In some embodiments according to the present invention, an inventive silylating reagent is used to protect the 5'- and 3'-hydroxy groups of a nucleoside, such as a ribonucleoside. Nucleosides according to the present invention include a nucleobase (often referred to in the art as a nucleosidic base or simply a base). The term nucleobase includes naturally occurring bases, such as adenine guanine, thymine, uridine and cytosine, and modified bases, such as 5-methylcytosine. As used herein, "unmodified" or "natural" nucleobases include the purine bases adenine (A) and guanine (G), and the pyrimidine bases thymine (T), cytosine (C) and uracil (U). The general term "nucleobase" also includes modified nucleobases, which in turn include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications,* pages 289–302, Crooke, S. T. and Lebleu, B$_x$. , ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B$_x$., eds.,*Antisense Research andApplications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Protected nucleoside and nucleoside analogs of the present invention can be subjected to transglycosylation reactions as taught by, e.g. A. I. Zinchenko, V. N. Barai, V. I. Lyachovez, E. I. Kvasyuk, I. A. Mikhailopulo, Bioorg. Khim. (Rus.) 1988, 14, 1401. The bis-silylating reagent of the present invention provides excellent protection for the 5'- and 3'-OH groups during the process in which one nucleobase is replaced by another by transglycosylation.

The inventive silylating agents are advantageously used to make nucleosides suitable as intermediates in the synthesis of oligonucleotides.

Nucleosides made by methods according to the present invention can be used in the synthesis of oligonucleotides. Oligonucleotides may be prepared using the nucleosides made by the methods of the present invention in at least three different processes. The first of these is the phosphoroamidite synthetic method described by Caruthers et al. (U.S. Pat. Nos. 4,500,707 and 4,973,679) and by Köster et al. (U.S. Pat. No. RE. 34,069). The second of these methods is by the H-phosphonate method taught by Froehler et al. (U.S. Pat. Nos. 5,548,076, 5,264,566, 4,959,463). The third is the phosphotriester approach taught by [German Offenlegenschrift 2,644,432].

Nucleic acids, e.g. ribonucleic acids, deoxyribonucleic acids, and modified ribonucleic acids (whether modified in the nucleobase or the sugar) that have been prepared by methods of the present invention may be used in oligonucleotide synthesis to prepare oligonucleotides via a variety of intermediates. For example, a 5'-O-protected nucleoside can be derivatized to form a monomer phosphoramidite, H-phosphonate or phosphotriester as described above and in the references cited. The monomer building blocks are then used to form oligonucleotides by methods described in the above cited references.

Such oligonucleotides are useful in various applications. For example some oligonucleotides are antisense compounds, which specifically hybridize with one or more nucleic acids encoding a target protein, such as a hematopoietic cell protein tyrosine kinase. As used herein, the terms "target nucleic acid" and "nucleic acid encoding hematopoietic cell protein tyrosine kinase" encompass DNA encoding hematopoietic cell protein tyrosine kinase, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of a target protein, such as a hematopoietic cell protein tyrosine kinase. In general, "modulation" means either an increase (stimulation) or a decrease (inhibition) in the expression of a gene.

It is preferred to target specific nucleic acids for antisense. "Targeting" an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. The targeting process also includes determination of a site or sites within this gene for the antisense interaction to occur such that the desired effect, e.g., detection or modulation of expression of the protein, will result. For example, in some contexts, an intragenic site may be the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In some contexts, "start codon" and "translation initiation codon" may refer to the codon or codons that are used in vivo to initiate translation of an mRNA molecule transcribed from a gene encoding hematopoietic cell protein tyrosine kinase, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect. In some contexts "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation. The target sites to which these preferred sequences are complementary are generally referred to as "active sites" and are therefore preferred sites for targeting.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds made by processes according to the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. In some cases, oligonucleotides made by process of the present invention can be 8 to about 50 nucleobases (i.e. from about 8 to about 50 linked nucleosides). Particularly preferred oligonucleotides antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Especially preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The term "2'-substituent" means H, OH or a group at the 2'-position other than H or OH. There are many such 2'-substituents known in the art, as discussed in more detail below in regard to sugar modifications. Included within the scope of 2'-substituents are 2'-O-substituted groups. The substituent group (i.e. 2'-O-substituent) of a 2'-O-substituted group may be a substituent known in the art, as described more fully herein in regard to sugar modifications. Exemplary 2'-O-substituents are alkyl, substituted alkyl, acyl or substituted acyl. Exemplary alkyl groups within the meaning of 2'-O-substituents are methyl, ethyl, etc. Exemplary substituted alkyl groups include methoxyethyl, aminoethyl, guanidinoethyl, etc.

Other sugar modifications include 2'-methoxy (2'-O—$CH_3$), 2'-aminopropoxy (2'-O$CH_2CH_2CH_2NH_2$) and 2'-O-allyl (2'-O—$CH_2$—CH=$CH_2$) and 2'-fluoro (2'-F). The 2'-modification may be in the arabino (up) position or ribo (down) position. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Modified oligonucleotides may also contain one or more substituted sugar moieties. Preferred oligonucleotides comprise one of the following at the 2' position: —OH (arabino); F (ribo- or arabino-); O—, S—, or N-alkyl; O—, S—, or N-alkenyl; O—, S— or N-alkynyl; or O-alkyl-O-alkyl, wherein the alkyl, alkenyl and alkynyl maybe substituted or unsubstituted $C_1$ to $C_{10}$ alkyl or $C_2$ to $C_{10}$ alkenyl and alkynyl. Particularly preferred are O[($CH_2$)$_n$O]$_m CH_3$, O($CH_2$)$_n$O$CH_3$, O($CH_2$)$_n NH_2$, O($CH_2$)$_n CH_3$, O($CH_2$)$_n$ONH$_2$, and O($CH_2$)$_n$ON[($CH_2$)$_n CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

Further sugar modifications include Locked Nucleic Acids (LNAs) in which the 2'-hydroxyl group is linked to the 3' or 4' carbon atom of the sugar ring thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B.$_x$, ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B.$_x$, eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resitance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al.,*Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structure of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Further down-stream processing of oligonucleotides made using processes according to the present invention may include admixing, encapsulating, conjugating or otherwise associating the oligonucleotides with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Oligonucleotide compounds made by processes of the present invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotide compounds made by processes according to the present invention can be utilized for diagnostics, therapeutics, prophylaxis and as research reagents and kits. For therapeutics, an animal, preferably a human, suspected of having a disease or disorder which can be treated by modulating the expression of hematopoietic cell protein tyrosine kinase is treated by administering antisense compounds in accordance with this invention. The compounds made by processes according to the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The oligonucleotide compounds made by processes according to the present invention are useful for research and diagnostics, because these compounds hybridize to nucleic acids encoding specific proteins, such as hematopoietic cell protein tyrosine kinase, enabling sandwich and other assays to easily be constructed to exploit this fact. Hybridization of the oligonucleotide compounds made by processes according to the present invention with a nucleic acid encoding a protein, such as hematopoietic cell protein tyrosine kinase, can be detected by means known in the art. Such means may include conjugation of an enzyme to the oligonucleotide, radiolabelling of the oligonucleotide or any other suitable detection means. Kits using such detection means for detecting the level of hematopoietic cell protein tyrosine kinase in a sample may also be prepared.

The present invention also includes pharmaceutical compositions and formulations which include the oligonucleotide compounds made by processes according to the present invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/ salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcamitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions made from oligonucleotide compounds made by processes according to the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations comprising oligonucleotide compounds made by processes according to the present invention of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The oligonucleotide compounds made by processes according to the present invention may be formulated into any of many possible dosage forms such as, but not limited to, tablets, capsules, gel capsules, liquid syrups, soft gels, suppositories, and enemas. The oligonucleotide compounds made by processes according to the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In some embodiments of the present invention pharmaceutical compositions comprising oligonucleotide compounds made by processes according to the present invention may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Compositions comprising the oligonucleotide compounds made by processes according to the present invention may be prepared and formulated as emulsions. Emulsions are typically heterogenous systems of one liquid dispersed in another in the form of droplets usually exceeding 0.1 $\mu$m in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In some embodiments of the present invention, the compositions comprising oligonucleotide compounds made by processes according to the present invention may be formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I(glyceryl dilaurate/cholesterol/polyoxyethylene-10-stearyl ether) and Novasom™ I(glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or ($B_x$) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

In some embodiments, the present invention may employ various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcamitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihycrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in viva processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The present invention may be further appreciated by the person having skill in the art by reference to the following illustrative, non-limiting examples of embodiments of the present invention.

EXAMPLES

The following designations are made in the following examples:

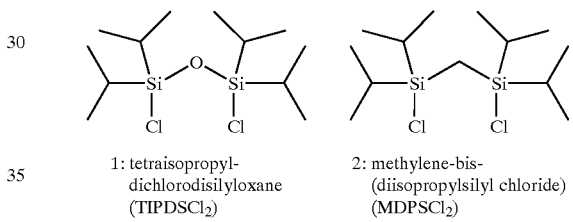

1: tetraisopropyl-dichlorodisilyloxane (TIPDSCl$_2$)

2: methylene-bis-(diisopropylsilyl chloride) (MDPSCl$_2$)

Example 1

Preparation of Inventive Compound 2

The synthesis of compound 2 is shown in Scheme 1. Commercially available silane 3 (Gelest, Tullytown Pa.) was converted to tetraalkylated silane 4 upon treatment with the appropriate Grignard reagent in the presence of catalytic CuCl$_2$. Chlorination of silane 4 was achieved in refluxing carbon tetrachloride using catalytic PdCl$_2$.[1] Following a filtration of the residual PdCl$_2$ under inert atmosphere, compound 2 was isolated after high vacuum distillation (113° C. at 1 mmHg) in 68% combined yield.

Scheme 1$^a$

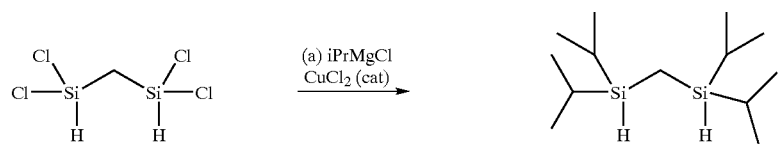

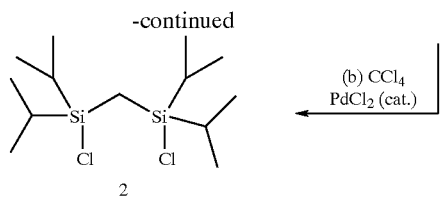

2

[a]reagents and conditions: (a) 4.4 equivalents of i_PrMgCl (2.0 M in THF), 0.01 equivalents CuCl$_2$ in THF, 65° C., 5 h, 78% yield; (b) 1.0 equivalent CCl$_4$, 0.02 equivalent PdCl$_2$, 60° C., 2 h, yield 87%.

Example 2

Preparation of 2'-MOE Guanosine

The application of disilane 2 to the synthesis of 2'-MOE-guanosine is summarized in Scheme 2. Treatment of 5 (guanosine) with a slight excess of disilane 2 (MDPSCl$_2$) in the presence of imidazole produced the desired 3',5' protected nucleoside 6 in 79% yield. The effects of different bases and temperature during the protection of 5 were also investigated. Among them, imidazole was found to produce optimal results. As compared to the similar protection with disilane 1, the reaction with 2 was significantly slower, presumably due to the decreased reactivity of the silyl chloride functionality. Nonetheless, the regioselectivity of the reaction was excellent and comparable to the one observed for 1. While not wishing to be bound by theory, it is presumed that this is attributable to the steric effects of the isopropyl groups that react initially with the 5'-hydroxyl group with 1,000/1 selectivity and subsequently with the neighboring 3'-hydroxyl unit.

The conversion of 6 to compound 7 was examined under a variety of alkylation conditions which are summarized in Table 1. Sodium hydride and potassium t-butoxide were found to lead to partial desilylation when the reaction was performed at 0–25° C. Similar results were obtained with CsOH. In contrast to the above conditions, use of BEMP as the base did not lead to desilylation but yielded predominantly N-alkylated adduct. Promising results were obtained when NaHMDS was examined as the base, leading predominantly to the desired alkylated product 7. This reaction was further improved by adding a catalytic amount of TBAI and performing the alkylation at −20° C. Under these optimized conditions, purified compound 7 was isolated in 85% yield. Interestingly, use of NaHMDS under the above conditions did not produce any N-alkylated adduct, thus eliminating the need to protect the nucleobase during alkylation. It is also worth mentioning that guanosine protected with disilane 1 underwent complete deprotection under the above conditions, supporting our hypothesis that the fragility of 1 derives from the presence of the oxygen atom. Moreover, exposure of alkylated adduct 7 to excess NaHMDS even at 25° C. did not yield any deprotected material, indicating that compound 7 is stable to any base-induced desilylation. This observation suggests that the desilylation observed with compound 6 under harsh conditions is due to the proximity effect of the neighboring C2'-alkoxide species.

TABLE 1

Effect of base during alkylation of 6

| Base (3.0 equiv) | Temp ° C. | TBAI | Results (6/5/7) |
|---|---|---|---|
| NaH | 25 | 0.1 eq | 7:3 |
| NaH | 0 | N/A | 8:2 |
| K t-butanol | 25 | 0.1 eq | 7:3 |
| BEMP | 25 | — | 0:0:9:1[a] |
| CsOH | 0 | — | 1:9 |
| LiHMDS | −20 | 0.3 eq | NR |
| KHMDS | −20 | 0.3 eq | 8:1 |
| NaHMDS | −10 | — | 8:1:1:1[b] |
| NaHMDS | −20 | 0.3 eq | 1:0:9[c] 85% 2'OMOE |

[a]N alkylation together with dialkylation were observed
[b]2'-MOE alkylated product and some cleaved material were formed
[c]A ratio of 1:9 of starting material/desired product was observed. After isolation compound 7 was obtained in 85% yield.

Scheme 2[a]

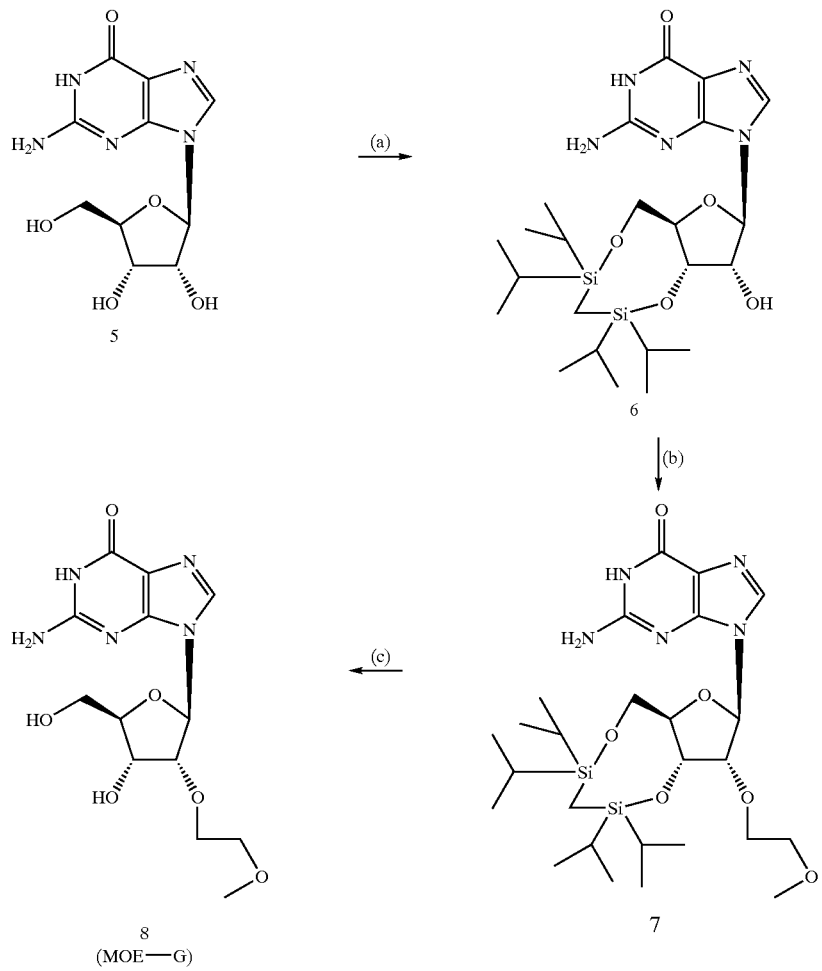

[a]Reagents and conditions: (a) 1.15 equivalent MDPSCl$_2$, 5.0 equivalent imidazole, in DMF, 0° to 25° C., 5 h, 79% yield; (b) 3.0 equivalent NaHMDS, 0.3 equivalent TBAI, 3.0 equivalent MeOCH$_2$CH$_2$Br, DMF, -20° C., 3 h, 85% yield; (c) 0.1 equivalent TBAF (1.0 M in THF), wet THF, 35° C., 5 h, 97% yield.

The fluoride-induced desilylation of 7 was slower than the one performed in the identical substrate protected with 1. Nonetheless, heating a solution of 7 in wet THF at 35° C. in the presence of 0.1 equivalents of TBAF produced substrate 8 in 97% yield.

Example 3

Preparation of bis(diisopropylbromosilyl)benzene

A method of preparing bis(diisopropylbromosilyl) benzene is shown in Scheme 3, below. In the first step, 1,2-dibromobenzene is reacted with Mg in THF, to form the Grignard reagent, which is then reacted with diisopropylchlorosilane to form 1,2-bis(diisopropylsilyl)benzene, which, in the second step, is reacted with CH$_2$Br$_2$ over PdCl$_2$ catalyst to form the 1,2-bis-(diisopropylbromosilyl)benzene product.

Scheme 3

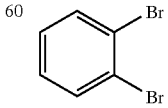
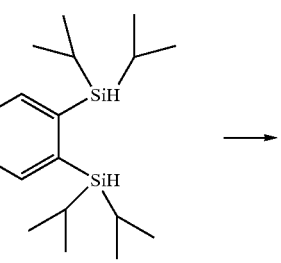

-continued

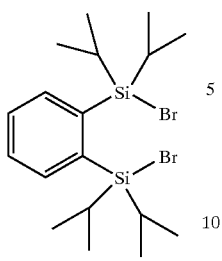

A more general method of synthesizing 1,2-bis(dialkylhalosilyl)aryl compounds is shown in Scheme 4.

Scheme 4

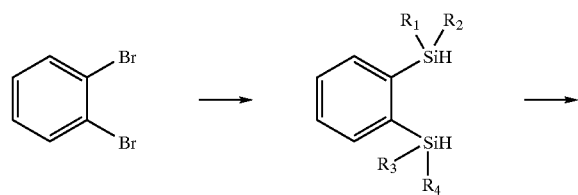

-continued

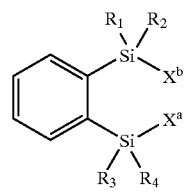

wherein $R_1$–$R_4$ are as defined herein, and $X^a$ and $X^b$ are leaving groups.

In the first step, the dibromobenzene (which may be replaced by 1,2-dichlorobenzene, 1-bromo-2-chlorobenzene, or other halogenated aryl compound, such as 1,3-dihalobenzene, 1,8-dihalonaphthylene, etc.) is reacted with Mg in the presence of a dialkylchlorosilane ($R_1R_2SiH$, $R_3R_4SiH$) to form a bis(dialkysilyl)benzene, which is then further reacted with $CH_2X^aX^b$ in the presence of a $PdCl_2$ catalyst to form the 1,2-bis(dialkylhalosilyl)aryl compound.

General preparative methods for 2'-MOE, 2'-deoxy and 2'-Me nucleosides are shown below in Scheme 5.

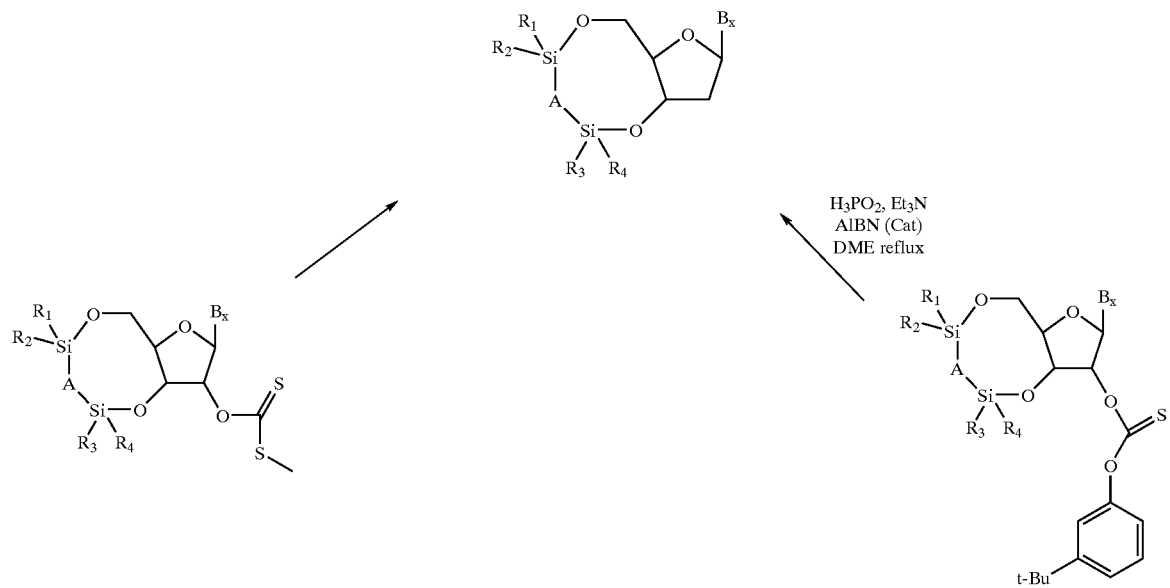

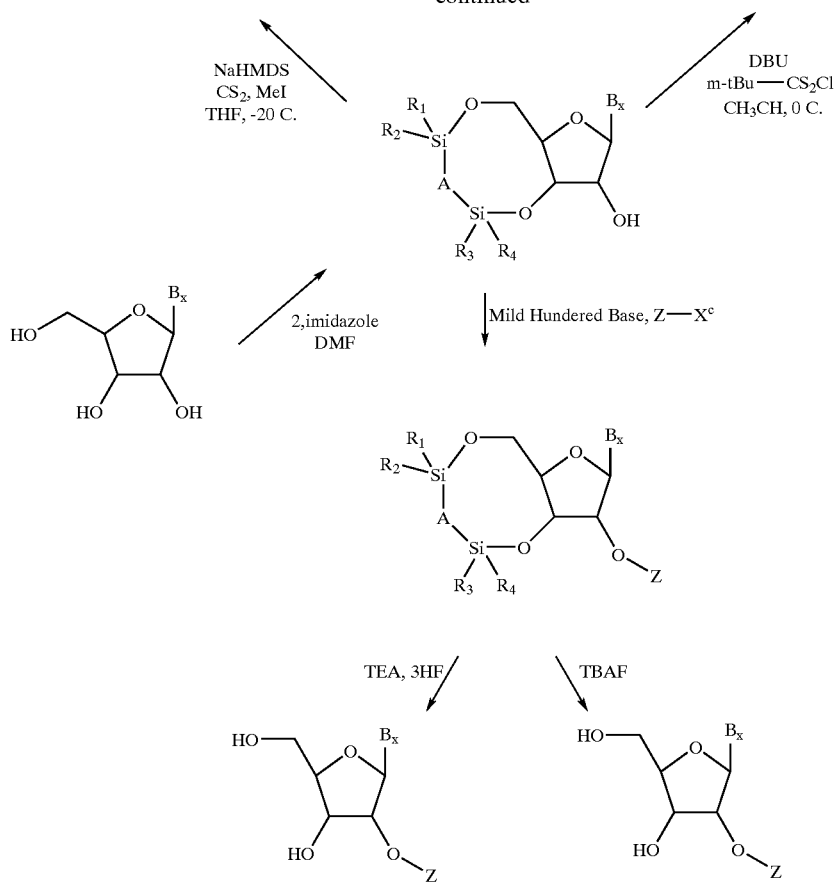

As shown in Scheme 5, a diprotected nucleoside is can be reacted with an alkyl group having a leaving group (Z—X$^c$) in the presence of a mild hindered base. The bis-silyl protective group can then be removed to produce the 2'-Z-modified nucleoside. $^a$Bx is a nucleobase, Z is a 2'-O-substituent, such as alkyl or substituted alkyl, A is a moiety other than oxygen, and $R_1$–$R_4$ are as defined herein.

The above general scheme has been applied to guanosine to make dG (deoxyguanosine), 2'-Me G (2'-methylguanosine) and 2'-MOE G (2'-methoxyethylguanosine) as depicted in Scheme 6, below.

Scheme 6$^a$

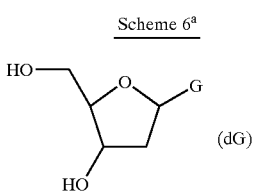

(dG)

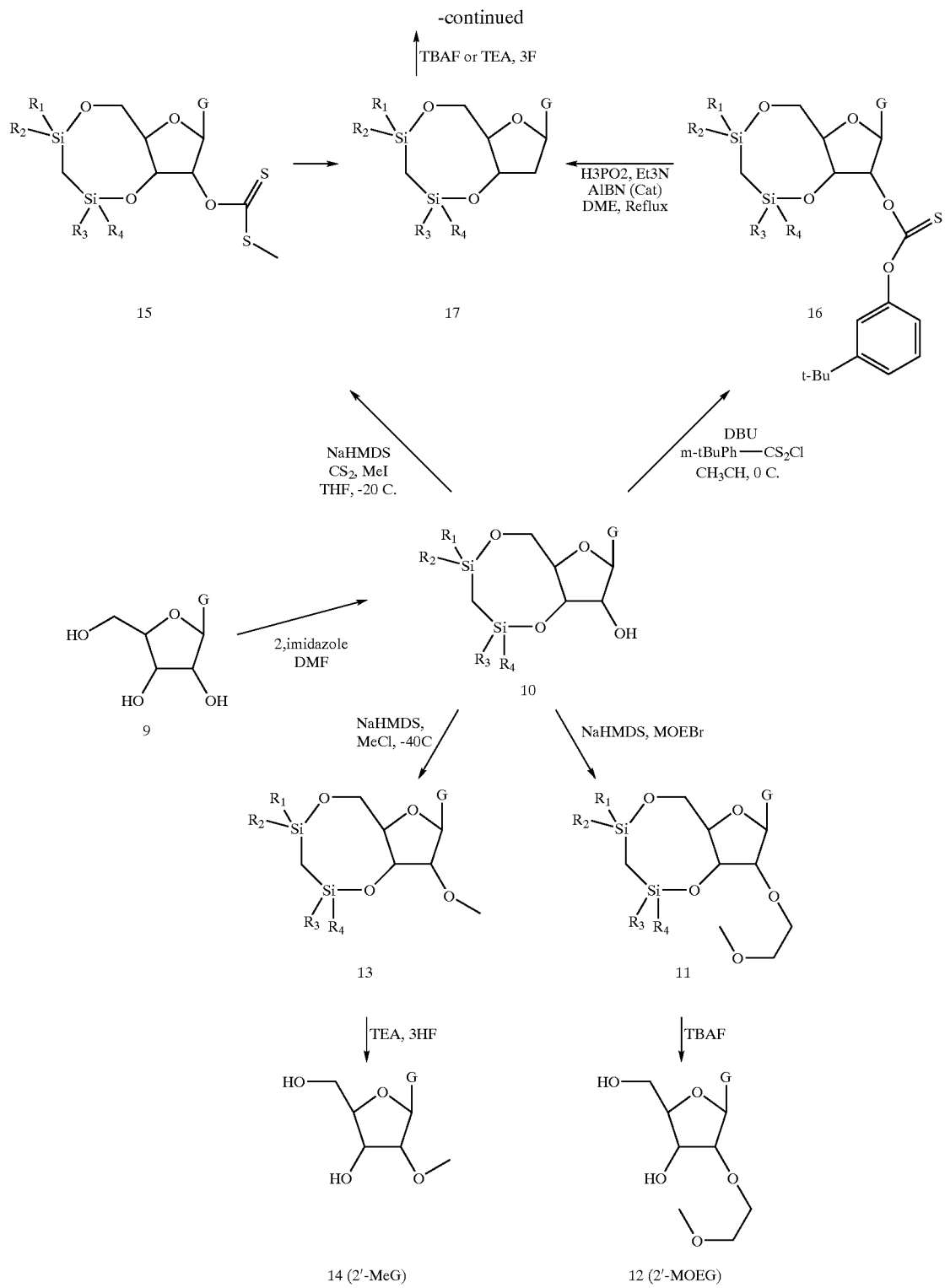

*G is the nucleobase guanine.

The application of disilane 2 to the synthesis of 2'-MOE-guanosine is summarized in Scheme 6. Treatment of guanosine with excess 2 (MDPSCl$_2$, a protective reagent of the present invention) in the presence of imidazole produced the desired 3',5'-diprotected intermediate in 79% yield. As compared with the similar protection with TIPDSCl$_2$, the reaction with 2 was somewhat slower. While not wishing to be bound by theory, it is believed that the decreased reactivity is due to the decreased reactivity of the silyl chloride functionality, which is believed to be attributable to the steric effects of the isopropyl groups. It is further believed that the 5'-hydroxyl group is first protected (1,000/1 selectivity) and subsequently the neighboring 3'-hydroxyl unit is protected. The conversion of the diprotected intermediate to the diprotected 2'MOE intermediate was examined under various alkylation conditions that are summarized in Table 1 below. Sodium hydride and potassium t-butoxide were found to lead to partial desilylation when the reaction was performed at −25° C. Similar results were obtained with CsOH. In contrast, used of BEMP as the based did not lead desilylation but yielded predominantly N-alkylated adducts. In contrast, suitable results were obtained with mild hindered bases, such as the sodium salt of hexamethyldisilazane (NaHMDS). Reaction of MOEBr ($CH_3OCH_2CH_2Br$) in the presence of NaHMDS led predominantly to the 2'-MOE-5',3'-diprotected guanosine intermediate. This reaction was further improved by addition of TBAI as a catalyst, and by conducting the reaction at −25° C. Under these conditions, purified 2'-MOE-5',3'-diprotected guanosine was isolated in 85% yield. Use of NaHMDS did not result in any N-alkylated adduct, thus eliminating the need to protect the nucleobase during alkylation. In contrast, guanosine protected with the $TIPDSCl_2$ underwent complete deprotection under the above conditions, thereby demonstrating the superiority of the inventive reagents as protecting agents for 2'-alkylation of nucleosides. The TBAF-induced deprotection (desilylation) of the protected 2'-MOE intermediate proceeded more slowly than that corresponding to $TIPDSCl_2$, however, heating a solution of the diprotected 2'-MOE intermediate in THF at 35° C. in the presence of 1 equivalent of TBAF produced the desired 2'-MOE guanosine produce in 97% yield. Heating the diprotected 2'-MOE intermediate in the presence of 0.6 equivalents of TBAF in wet THF at 50° C. resulted in a 90% yield after 24 h.

The methylation of 6 was examined under various alkylation conditions, which are summarized in Table 2. Use of sodium hydride and potassium t-butoxide led to partial desilylation when the reaction was performed between 25 to −25° C., while at lower temperatures the reaction was incomplete even after 12 hours. Improved results were obtained when a mild hindered base such as NaHMDS was used as the base, leading to a mixture of desired compound and a side-product arising from methylation of the nucleobase. Switching the electrophile from methyl iodide (MeI) to methyl chloride (MeCl) resulted in suitable results, whereby diprotected 2'-Me nucleoside was produced in 86% yield. The combination of NaHMDS as the base and methyl chloride as the electrophile at −40 to −25° C. did not produce any N-alkylated adduct, thus eliminating the need to protect the nucleobase during methylation.

TABLE 2

Methylation of compound diprotected guanosine

| Base | Alkylating agent | Temp° C. | Results (10/9/13) |
|---|---|---|---|
| NaH | MeI | 0 | 3:2:0:5[a] |
| NaHMDS | MeI | −20 | 0:2:4:4[a] |
| LiHMDS | MeI | −40 | 0:0:0:10[b] |
| KHMDS | MeI | −40 | 5:0:2:3[a] |
| NaHMDS | $(CH_3O)_2SO_2$ | −40 | 0:5:0:5[b] |
| NaHMDS | $(CH_3O)_2P(O)H$ | 60 | NR |
| Pyridine | $CF_3SO_3CH_3$ | 25 | NR |
| NaHMDS | $CH_3Cl$ in t-butyl methyl ether | −40–27 | 1:0:1 |
| NaHMDS | $CH_3Cl(g)$ | −40–27 | 1:0:9[c] 86% 2'OMe |

[a]N alkylation together with dialkylation were observed
[b]N alkylation

Preparative Examples

All reagents were commercially obtained (Aldrich, Acros) at highest commercial quality and used without further purification except where noted. Air- and moisture-sensitive liquids and solutions were transferred via syringe or stainless steel cannula. Organic solutions were concentrated by rotary evaporation below 45° C. at about 20 mmHg. All nonaqueous reactions were carried out using oven-dried glassware, under an argon atmosphere in dry, freshly distilled solvents under anhydrous conditions, unless otherwise noted. Tetrahydrofuran (THF) and diethyl ether ($Et_2O$) were distilled from sodium/benzophenone; dichloromethane ($CH_2Cl_2$) and toluene from calcium hydride; and benzene from potassium. Guanosine (5) was purchased from Sigma and was azeotropically dried with pyridine under vacuum before use. Silane 3 was purchased from Gelest, Tullytown Pa. and used without any further purification. Yields refer to chromatographically and spectroscopically ($^1H$ NMR) homogeneous materials, unless otherwise stated. Reactions were monitored by thin-layer chromatography carried out on 0.25 mm E. Merck silica gel plates (60F-254) using UV light as visualizing agent and 7% ethanolic phosphomolybdic acid, or p-anisaldehyde solution and heat as developing agents. E. Merck silica gel (60, particle size 0.040–0.063 mm) was used for flash chromatography. Preparative thin-layer chromatography separations were carried out on 0.25 or 0.50 mm E. Merck silica gel plates (60F-254). NMR spectra were recorded on Varian Mercury 300, 400 and/or Unity 500 MHz instruments and calibrated using residual undeuterated solvent as an internal reference. The following abbreviations were used to explain the multiplicities: s=singlet; d=doublet, t=triplet, q=quartet, m=multiplet, b=broad. IR spectra were recorded on a Nicolet 320 Avatar FT-IR spectrometer and values are reported in $cm^{-1}$ units. Optical rotations were recorded on a Jasco P-1010 polarimeter. High resolution mass spectra (HRMS) were recorded on a VG 7070 HS mass spectrometer under chemical ionization (CI) conditions or on a VG ZAB-ZSE mass spectrometer under fast atom bombardment (FAB) conditions.

Bis(diisopropylsilyl)methane (4): A solution of bis (dichlorosilyl)methane (3) (10.0 g, 0.05 mol) and $CuCl_2$ (100 mg, 0.74 mmol) in 100 ml THF was treated with isopropyl magnesium chloride (2.0 M in THF, 103 mL, 0.206 mol) added dropwise at 25° C. over a period of 2 hours. After the addition, the mixture was refluxed for 5 h. 300 ml of water was then added and the organic phase was separated. The aqueous phase was extracted with hexanes (2×50 ml) and the combined organic phases were washed with water, and brine, and dried over $MgSO_4$. The organic solvents were evaporated under reduced pressure and the residue was filtered through a 10 cm thick silica gel column using hexane as the eluant to afford product 4 (8.9 g, 0.029 mol, 78% yield).

Bis(diisopropylchlorosilyl)methane using $CCl_4$ as chlorinating reagent (2): To a mixture of bis(diisopropyl-silyl) methane (4) (5.0 g, 0.02 mol) and $PdCl_2$ (72.6 mg, 0.41 mmol) was added dry $CCl_4$ (1.98 mL, 0.021 mol) in one portion. The reaction was kept under argon at 60° C. for 2 h. The $PdCl_2$ was filtered under argon, and the resulting mixture was distilled under reduced pressure to produce compound 2 (5.6 g, 0.02 mol, 87% yield) as a clear liquid. 2: $^1H$ NMR (400 MHz, benzene) ☐ 1.02–1.17 (m, 28H), 0.28 (d, J=0.8 Hz, 2H).

Bis(diisopropylchlorosilyl)methane using $CHCl_3$ as the chlorinating reagent: An oven-dried, one-necked, round-bottomed 250 mL flask was filled with argon and equipped with a magnetic stirring bar was connected to an oven-dried, argon filled 100 mL drop funnel. The flask was charged with bis(diisopropylsilyl)methane (60 g, 0.246 mol) and $PdCl_2$ (870 mg, 4.92 mmol) whereas the funnel was charged with anhydrous CHCl₃ (29.3 g, 0.248 mol). The reaction vessel was then placed in an oil bath with CHCl₃ added dropwise to the reaction mixture. After complete addition of CCl₄, the reaction mixture was kept at 60° C. under argon for 2 hours. The mixture was then distilled under high vacuum to afford bis(diisopropylchlorosilyl)methane (65.6 g, 0.209 mol, 85.1%).

Bis(diisopropylbromosilyl)methane: An oven-dried, one-necked, round-bottomed 100 mL flask was filled with argon and equipped with a magnetic stirring bar was connected to an oven-dried, argon filled 100 mL drop funnel. The flask was charged with bis(diisopropylsilyl)methane (20 g, 0.082 mol) and PdCl₂ (290 mg, 1.64 mmol) whereas the funnel was charged with anhydrous CH₂Br₂ (15.7 g, 0.09 mol). The reaction vessel was then placed in an oil bath with CH₂Br₂ added dropwise to the reaction mixture. After complete addition of CH₂Br₂, the reaction mixture was kept at 60° C. under argon for 1 hour. The mixture was then distilled under high vacuum to afford bis(diisopropylbromosilyl)methane (31.1 g, 0.077 mol, 94%).

1,2-Bis(diisopropylsilyl)benzene: 2.0 g of magnesium and 10 g of diisopropyl-chlorosilane were mixed in 80 ml dry THF and treated with 8.3 g of o-dibromobenzene (6) added dropwise. The mixture was refluxed for 45 h and then cooled to room temperature. 200 ml of water was added and the organic phase was separated. The aqueous phase was back extracted by hexanes (3×50 ml). The combined organic phases were washed with water, brine and dried using MgSO₄. The solvent was evaporated, and the residue was purified by column chromatography using hexane as an eluant to produce 6.9 g of compound 7 (69% yield).

1,2-Bis(diisopropylbromosilyl)benzene: To a mixture of 5 g of 1,2-bis(diisopropylsilyl)-benzene and 0.02 equal molar of PdCl₂ was added in one portion 2 molar equivalents of dry CH₂Br₂. The reaction was kept at 60° C. for 1 h under argon. The PdCl₂ was filtered under argon and the residue was dried under high vacuum to afford 7.2 g of 1,2-bis (diisopropyl-bromosilyl)benzene (95% yield).

Compound 6: Guanosine (1.0 g, 0.0035 mol) and imidazole (1.13 g, 0.017 mol) were dried by co-evaporation of 2 ml pyridine, then dissolved in 20 ml dry DMF, and treated with 2 (1.27 g, 0.0004 mol) added dropwise at 0° C. The temperature was gradually increased to 25° C. After 5 h of reaction, TLC showed no further change. The reaction mixture was poured into ice-water, and the precipitated white solid was filtered to afford compound 6 (1.36 g, 0.0026 mol, 79% yield). 6: ¹H NMR (400 MHz, DMSO) δ 10.61 (s, 1H), 7.76 (s, 1H), 6.48 (s, 2H), 5.67 (s, 1H), 5.47 (d, J=4.4 Hz, 1H), 4.24 (dd, J=3.6, 8.0 Hz, 1H), 4.13 (t, J=4.4 Hz, 1H), 4.01 (t, J=3.6 Hz, 1H), 3.90 (d, J=8.4 Hz, 1H), 3.77–3.81 (m, 1H), 0.96–1.06 (m, 28H), 0.02 (s, 2H); HRMS, calcd for $C_{23}H_{41}N_5O_5Si_2$ (M+H⁺) 524.2719, found 524.2699.

Compound 7: To a solution of compound 6 (2.01 g, 0.004 mol) in 60 mL DMF at −20° C. was added BrCH₂CH₂OCH₃ (1.08 mL, 0.005 mol), sodium bis(trimethylsilyl)amide (1.0 M in THF, 11.5 mL, 0.01 15 mol) and TBAI (423 mg, 0.001 mol) and the mixture was stirred for 4 hours under argon. After quenching the reaction with methanol, the product was precipitated in ice to produce compound 7 (1.89 g, 0.004 mol, 85% yield). 7: ¹H NMR (400 MHz, DMSO) □ 10.67 (s, 1H), 7.74 (s, 1H), 6.48 (s, 2H), 5.73 (s, 1H), 4.35 (dd, J=4.6, 9.2 Hz, 1H), 4.10 (d, J=4.8 Hz, 1H), 4.03 (d, J=11.4 Hz, 1H), 4.00–3.84 (m, 3H), 3.68–3.84 (m, 2H), 3.40–3.52 (m, 1H), 3.45 (s, 3H), 0.96–1.10 (m, 28H), 0.00–0.10 (m, 2H); ¹³C NMR (400 MHz, CDCl₃) d 156.64, 153.76, 150.33, 134.12, 116.64, 86.57, 81.96, 80.49, 71.42, 70.37, 70.03, 60.56, 58.15, 18.09, 18.03, 17.86, 17.66, 17.63, 17.59, 17.50, 17.44, 13.91, 13.86, 13.82, 13.79, −9.42; HRMS, calcd for $C_{26}H_{47}N_5O_6Si_2$ (M+Na⁺) 604.2957, found 604.2983.

2'-O-MOE G (8): To a solution of compound 7 (50 mg, 0.086 mmol) in THF and water at 25° C. were added TBAF (1 M in THF, 0.009 mL, 0.009 mmol) and the mixture was stirred at 35° C. for 5 hours. The solvent was then evaporated under reduced pressure and the residue was filtered in a short pad of silica gel using 10% methanol in dichloromethane to afford compound 8 (28 mg, 0.082 mmol, 97% yield). 8: ¹H NMR (400 MHz, DMSO) □ 10.68 (s, 1H), 7.95 (s, 1H), 6.50 (s, 2H), 5.78 (d, J=6.0 Hz, 1H), 5.08 (d, J=5.2 Hz, 2H), 4.33 (d, J=6.0 Hz, 1H), 4.23 (d, J=3.2 Hz, 1H), 3.88 (d, J=3.2 Hz, 1H), 3.65 (m, 3H), 3.52–3.57 (m, 2H), 3.35 (s, 3H), 3.38–3.40 (m, 1H).

The methylation of 6 was examined under various alkylation conditions, which are summarized in Table 2. Use of sodium hydide and potassium t-butoxide led to partial desilylation when the reaction was performed between 25 to −25° C., while at lower temperatures the reaction was incomplete even after 12 hours. Improved results were obtained when a mild hindered base such as NaHMDS was used as the base, leading to a mixture of desired compound and a side-product arising from methylation of the nucleobase. Switching the electrophile from methyl iodide (MeI) to methyl chloride (MeCl) resulted in suitable results, whereby diprotected 2'-Me nucleoside was produced in 86% yield. The combination of NaHMDS as the base and methyl chloride as the electrophile at −40 to −25° C. did not produce any N-alkylated adduct, thus eliminating the need to protect the nucleobase during methylation.

Compound 13: To a solution of compound 10 (200 mg, 0.4 mmol) in 6.0–8.0 mL DMF at 40° C. was added MeCl₍g₎ 0.4 mmol) (bubble into the reaction mixture for 2–2.5 minutes, approximately 7.5–10.0 g), sodium bis(trimethylsilyl)amide (1.0M in THF, 1.15 mL, 1.15 mmol) and the mixture was stirred for 4.5 hours with gradual increase in temperature to −27° C. under argon. After quenching the reaction with methanol, the product was precipitated in ice to produce compound 13 (175 mg, 3.3 mmol, 86% yield). 13: ¹H NMR (400 MHz, DMSO) □ 10.73 (s, 1H), 7.79 (s, 1H), 6.55 (b, s, 2H), 5.74 (s, 1H), 4.34 (dd, J=3.9, 9.0 Hz, 1H), 4.05 (d, J=12.0 Hz, 1H), 3.93 (d, J=4.8 Hz, 1H), 3.89 (d, J=8.8 Hz, 2H), 3.40 (s, 3H, OCH₃), 0.93–1.10 (m, 28H), 0.03 (s, 2H); ¹³C NMR (400 MHz, CDCl₃)□□ 159.30, 153.09, 150.47, 134.98, 117.09, 87.92, 84.13, 81.39, 69.95, 60.67, 59.68, 18.15, 18.02, 17.99, 17.96, 17.92, 17.86, 14.67, 14.62, 14.57, 14.46, 14.35, −9.44; HRMS, calcd for $C_{24}H_{43}N_5O_5Si_2$ (M+Na⁺) 560.2695 found 560.2688.

Compound 14: To a solution of compound 13 (50 mg, 0.093 mmol) in THF were added TEA.3HF (0.015 mL, 0.092 mmol) and the mixture was stirred at room temperature for 24–26 hours. The solvent was then evaporated under reduced pressure and the residue was collected to afford compound 14 (26 mg, 0.084 mmol, 89% yield). 14: ¹H NMR (400 MHz, DMSO) □ 10.65 (s, 1H), 7.90 (d, J=31.2 Hz, 1H), 6.51 (s, 2H), 5.77 (dd, J=9.6, 12 Hz, 1H), 5.13 (s, 1H), 5.08 (s, 1H), 4.47 (s, 1H), 4.32 (s, 1H), 4.11 (t, J=55.2 Hz, 1H), 3.85 (d, J=18.4 Hz, 2H), 3.55 (d, J=18 Hz, 3H); ¹³C NMR (125 MHz, DMSO) □ 156.87, 154.01, 151.35, 135.34, 116.59, 85.94, 84.34, 82.78, 68.70, 61.32, 57.51.

Compound 15: 100 mg of guanosine derivative 10 were dissolved in 2.0 ml dry THF and treated with 2.2 molar equivalents of NaHMDS at −20-C, followed by 2 molar equivalents of CS2 and 1.5 molar equivalents of CH$_3$I. After 15 minutes, the reaction was quenched with 1.0 M HCl. After evaporation of the solvent, the product was purified by column chromatography to afford 94 mg of compound 15 (80% yield).

Compound 16: A solution of 10 (1.0 g, 1.91 mmol) in acetonitrile (15 ml) was cooled to 0° C., 1,8-diazabicyclo[5.4.0]undec-7-ene (DBU, 639 mg, 4.21 mmol) was added. The m-t-butyl-phenylchlorothioformate (523 mg, 2.29 mmol) was added in 5 min. The reaction was then stirred at room temperature for 5 h. The mixture was then concentrated under vacuum to remove acetonitrile and the residue was purified by column chromatography using dichloromethane/methanol 95:5 to afford the desired product (997 mg, 1.396 mmol, 73%).16: $^1$H NMR (400 MHz, d$_6$-DMSO) □: 10.75 (s, 1H), 7.93 (s, 1H), 7.41–7.33 (m, 2H), 7.09–7.08 (m, 1H), 6.97–6.95 (m, 1H), 6.42 (s, 2H), 6.15–6.13 (m, 1H), 6.061–6.047 (d, 2H J=1.6), 4.80–4.76 (m, 1H), 3.99–3.86 (m, 3H), 1.24–1.15 (m, 9H), 1.13–0.99 (m, 28H), 0.16 (d, 1H J=14.4), 0.03 (d, 1H J=14.4). $^{13}$C NMR (400 MHz, d$_6$-DMSO) □: 194.06, 157.26, 154.53, 153.56, 153.41, 151.20, 136.07, 130.07, 124.29, 119.23, 119.03, 117.35, 85.41, 84.63, 81.86, 71.20, 61.95, 35.26, 31.57, 18.51, 18.44, 18.42, 18.32, 18.27, 18.24, 18.13, 15.00, 14.62, 14.56, −8.27.

Compound 17: To a solution of above product (120 mg, 0168 mmol) in DME (1.0 ml) were added Et$_3$N (0.262 ml, 1.88 mol) and 50% aqueous H$_3$PO$_2$ (0.175 ml, 1.67 mmol). This mixture was heated until reflux and AIBN (16.8 mg, 0.102 mmol) dissolved in DME (0.52 ml) was added in four portions (30 min. between each addition).

After 2.5 h reflux, the reaction mixture was cooled to room temperature, treated with dichloromethane (6 ml) and water (6 ml). The organic layer was washed via brine and concentrated under reduced pressure. The residue was column chromatographically purified giving the desired compound (54.5 mg, 0.108 mmol, 64%). $^1$H NMR (400 MHz, d6-DMSO) □: 10.62 (s, 1H), 7.82 (s, 1H), 6.45 (s, 2H), 6.05–6.02 (m, 1H), 4.56–4.52 (m, 1H), 3.82 (d, 2H J=4), 3.67–3.65 (m, 1H), 1.13–0.98 (m, 28H), 0.08 (d, 1H J=14), −0.02 (d, 1H J=14). $^{13}$C NMR (400 MHz, d$_6$-DMSO) □: 157.04, 154.05, 151.92, 135.02, 116.97, 84.17, 81.18, 81.37, 62.55, 18.46, 18.28, 18.22, 18.16, 18.10, 18.01, 14.61, 14.48, 14.22, 14.08, −8.52. Mass (MALDI-FTMS), MNa$^+$ 530.2577.

SUMMARY

The present invention provides an improved procedure for the synthesis of 2'-MOE-guanosine (8). For comparison purposes it is interesting to note that this procedure affords compound 8 from guanosine 5 in 3 steps and 65% yield, while all previously reported methods require several more steps and much lower yields. The present inventors are the first to recognize that the limitations of the previously reported methods are due to the fragility of the silicon-based protecting groups, such as 1, under the basic conditions required for alkylation. As compared to 1, inventive silane 2, upon protection of the nucleoside, was found to be more robust than 1 parent silane and withstood the alkylation conditions. An additional advantage of the inventive silane 2 over the conventional silane 1 is that the inventive silane 2 provides compounds that are highly crystalline and are easily purified by precipitation. This improvement has potentially major import with respect to scale-up and preparation of therapeutics.

Other uses and advantages of the inventive silylating reagents and methods will become apparent to the person of skill in the art upon consideration of the foregoing description and the following claims.

All references cited herein are expressly incorporated herein in their entirety.

While the present invention has been described with specificity in accordance with certain of its preferred embodiments, the following examples serve only to illustrate the invention and are not intended to limit the same.

We claim:

1. A process of protecting the 5'- and 3'-positions of a precursor, said precursor being a nucleic acid having the formula:

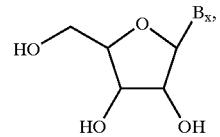

wherein B$_x$ is a nucleobase,
said process comprising contacting said compound with a silylating reagent of the formula:

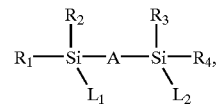

wherein R$_1$, R$_2$, R$_3$ and R$_4$ are independently a' lower alkyl, each of L$_1$ and L$_2$ is independently a leaving group, and A is a lower alkylene, phenylene or naphthylene,
for a time and under conditions suitable to protect the 5'- and 3'-positions of the nucleic acid, whereby a protected intermediate is formed, said protected intermediate having the formula:

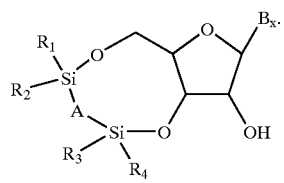

2. The process of claim 1, wherein B$_x$ is a naturally occurring, or protected nucleobase.

3. The process of claim 1, wherein B$_x$ is a member of the group consisting of guanine, adenine, thymine, cytosine, 5-methyl cytosine and uracil, or a protected version thereof.

4. The process of claim 1, wherein B$_x$ is guanine.

5. The process of claim 1, wherein R$_1$, R$_2$, R$_3$ and R$_4$ are independently methyl, ethyl, n-propyl, isopropyl, n-butyl, isobutyl, t-butyl or s-butyl.

6. The process of claim 1, wherein at least one of R$_1$, R$_2$, R$_3$ and R$_4$ is different from the others.

7. The process of claim 1, wherein each of R$_1$, R$_2$, R$_3$ and R$_4$ is isopropyl.

8. The process of claim 1, wherein A is a lower alkylene.

9. The process of claim 1, wherein A is methylene.

10. The process of claim 1, wherein A is phenylene or naphthylene.

11. The process of claim 1, wherein A is 1,8-naphthylene.

12. The process of claim 1, wherein A is 1,2-phenylene.

* * * * *

UNITED STATES PATENT AND TRADEMARK OFFICE
CERTIFICATE OF CORRECTION

PATENT NO. : 6,800,751 B2
APPLICATION NO. : 10/120649
DATED : October 5, 2004
INVENTOR(S) : Yogesh S. Sangvhi et al.

It is certified that error appears in the above-identified patent and that said Letters Patent is hereby corrected as shown below:

On the title page:
Item [56], References Cited, OTHER PUBLICATIONS, "Grøtli" reference, please delete "2'0-alkylguanosine" and insert therefor -- 2'-0-alkylguanosine --;

Item [56], References Cited, OTHER PUBLICATIONS, "Zielinski" reference, please delete "3'-amino-3'deoxy-nucleotides" and insert therefor
-- 3'-amino-3'-deoxy-nucleotides --.

Signed and Sealed this

Nineteenth Day of February, 2008

JON W. DUDAS
*Director of the United States Patent and Trademark Office*